Figure 1:
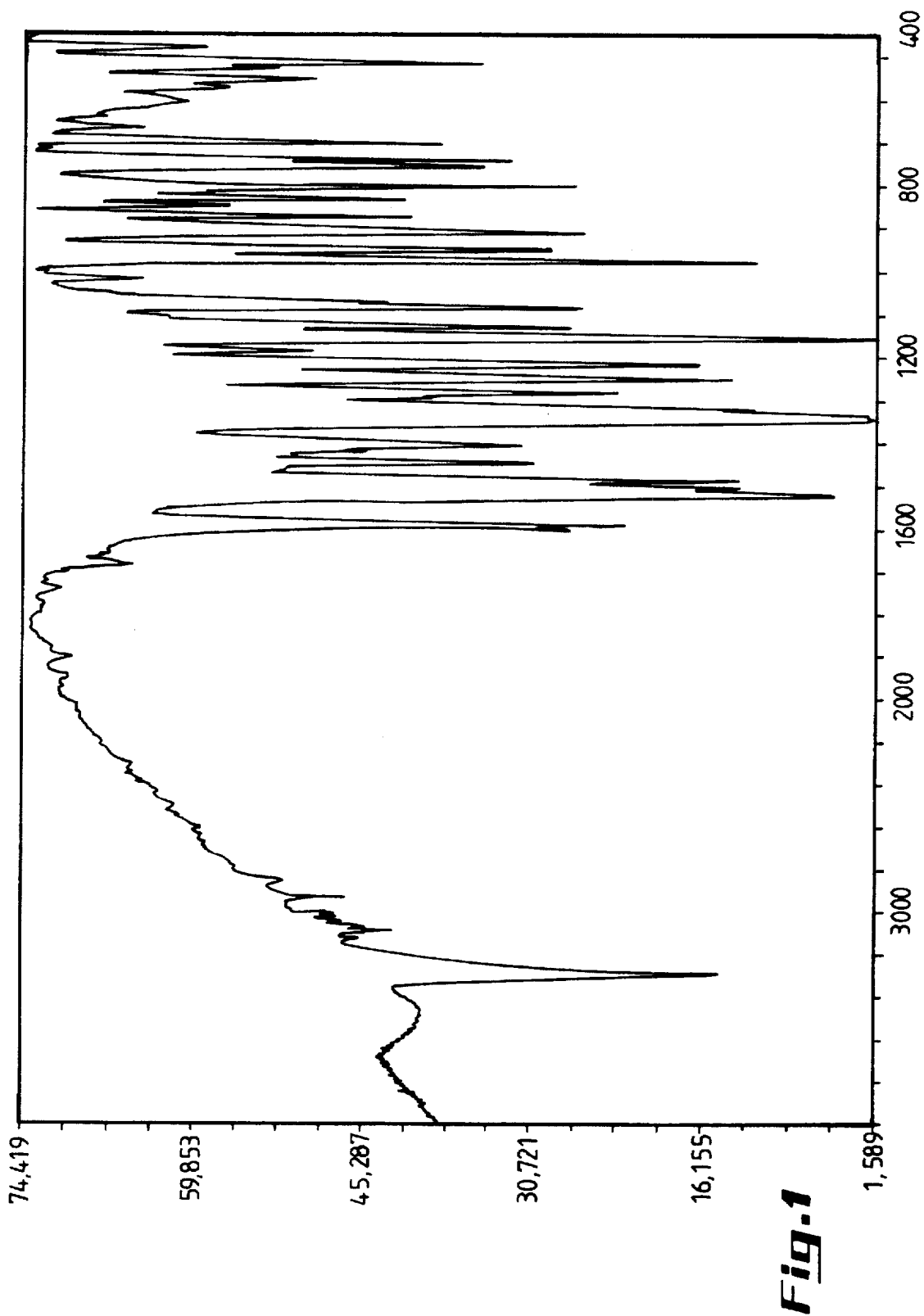

:

United States Patent [19]

Pirotte et al.

[11] Patent Number: 5,756,546
[45] Date of Patent: May 26, 1998

[54] WATER-SOLUBLE NIMESULIDE SALT AND ITS PREPARATION, AQUEOUS DOLUTION CONTAINING IT, NIMESULIDE-BASED COMBINATIONS AND THEIR USES

[76] Inventors: Bernard Pirotte, rue Tollet 5, 4680 Oupeye; Géraldine Piel, Quai de la Boverie 41, 4020 Liège; Philippe Neven, rue Neuve 11, 4460 Grâce-Hollogne; Isabelle Delneuville, rue Henri Delvaux 34, 4430 Ans; Joszef Geczy, avenue de Wolvendael 21, Boîte 6, 1180 Brussels, all of Belgium

[21] Appl. No.: 596,348
[22] PCT Filed: Jun. 16, 1995
[86] PCT No.: PCT/BE95/00055
§ 371 Date: Jun. 11, 1996
§ 102(e) Date: Jun. 11, 1996
[87] PCT Pub. No.: WO95/34533
PCT Pub. Date: Dec. 21, 1995

[30] Foreign Application Priority Data

Jun. 16, 1994 [BE] Belgium ................. 09400582

[51] Int. Cl.$^6$ ............................................. A61K 31/18
[52] U.S. Cl. ..................... 514/605; 514/601; 514/886; 564/89
[58] Field of Search ................. 514/605, 601, 514/886; 564/89

[56] References Cited

U.S. PATENT DOCUMENTS

| 3,840,597 | 10/1974 | Moore et al. | 260/556 F |
| 4,983,628 | 1/1991 | Frenette et al. | 514/510 |
| 5,019,563 | 5/1991 | Hunter et al. | 514/58 |

FOREIGN PATENT DOCUMENTS

91/17774  11/1991  WIPO.

*Primary Examiner*—Gary Geist
*Assistant Examiner*—Sreeni Padmanabhan
*Attorney, Agent, or Firm*—Birch, Stewart, Kolasch & Birch, LLP

[57] ABSTRACT

Water-soluble nimesulide salt consisting of the product of reaction of nimesulide and of L-lysine and its preparation, aqueous solution containing it, nimesulide-based combinations with cyclodextrins and their uses.

18 Claims, 28 Drawing Sheets

WATER-SOLUBLE NIMESULIDE SALT AND ITS PREPARATION, AQUEOUS DOLUTION CONTAINING IT, NIMESULIDE-BASED COMBINATIONS AND THEIR USES

This is the U.S. National Stage Application of PCT/BE95/00055 filed Jun. 16, 1995 now WO95/34533 published Dec. 21, 1995.

The present invention relates to a water-soluble nimesulide salt and its preparation, an aqueous solution containing it, nimesulide-based combinations with cyclodextrins, and the uses of these nimesulide salt [sic], aqueous solution and nimesulide-based combinations.

As is known, nimesulide, also known under the name of N-(4-nitro-2-phenoxyphenyl)methanesulfonamide or 4-nitro-2-phenoxymethanesulfonanilide, is a well known medication employed in the treatment of inflammatory diseases or disorders, such as, for example, rheumatic disorders and acute inflammations. However, it has the disadvantage of being very poorly soluble in water, and this opposes its use in some galenic applications such as drinkable and injectable solutions and some other oral preparations, such as effervescent tablets or granules. Furthermore, it is known that nimesulide salts in solution which are known so far, in particular the sodium salt, impose a relatively alkaline pH of which it is necessary to be aware when they are formulated in an injectable form. Moreover, the sodium salt of nimesulide, although soluble, has the disadvantage of releasing sodium ions therewith, which are often contraindicated. It is also known, in accordance with patent applications WO91/17774 and 94/02177, to be able to complex nimesulide with cyclodextrins but, in fact, the latter allow only a moderate increase in the solubility in water of nimesulide which is not in salt form, that is to say of the order of approximately 0.05 mg/ml (value determined by a solubility diagram), that is 5 times the solubility of nimesulide (0.01 mg/ml).

The aim of the present invention is to overcome these disadvantages and to provide a nimesulide salt which is highly soluble in water, which can be used especially for the preparation of drinkable or injectable solutions of nimesulide while preserving the pharmacological and/or therapeutic antiinflammatory applications of acidic nimesulide.

To this end, in accordance with the invention, the salt consists of the product of reaction of nimesulide and of L-lysine.

The salt advantageously contains approximately 1 mole of L-lysine per mole of nimesulide.

In accordance with an advantageous embodiment an aqueous solution of said salt of nimesulide is provided in combination with L-arginine, the weight ratio of the nimesulide salt to the L-arginine being advantageously approximately 1/1.

The invention also relates to nimesulide-based combinations in order to appreciably increase further the water-solubility of nimesulide in comparison with the nimesulide-L-lysine salt.

With this in mind, nimesulide and L-lysine are combined, in accordance with the invention, with at least one cyclodextrin, in the form of a mixture of these compounds, of a mixture of the nimesulide-L-lysine salt with cyclodextrin, of a nimesulide-cyclodextrin complex mixed with L-lysine or else of a nimesulide-L-lysine-cyclodextrin complex.

According to another advantageous embodiment of the invention the cyclodextrin is chosen from the group including α-, β- and γ-cyclodextrins, their hydrates, their derivatives and their mixtures.

Finally, the invention also relates to the preparation of the abovementioned nimesulide salt and to its applications and to the applications of the aqueous solution containing it and of the abovementioned combinations.

According to one embodiment, nimesulide and L-lysine are dissolved in methanol and the methanol is removed from the mixture thus obtained by conventional methods such as concentration by evaporation, followed by filtration, the methanol employed for dissolving the nimesulide being heated preferably to a temperature close to its boiling point, advantageously to a temperature of 54° to 64° C.

As just explained, the water-soluble nimesulide salt of the present invention consists of the product of reaction of nimesulide with the amino acid L-lysine in its non-salt monohydrate form. This salt of nimesulide and L-lysine or nimesulide-L-lysine salt contains 1 mole of L-lysine per mole of nimesulide. It is advantageous to comply with the mole-to-mole ratio of nimesulide and of L-lysine when preparing the salt in methanolic solution because if a departure is made therefrom any excess of either partner in the acid-base reaction is a source of contamination of the final product. The acid-base reaction for the preparation of the nimesulide-L-lysine salt is in accordance with the following reaction scheme:

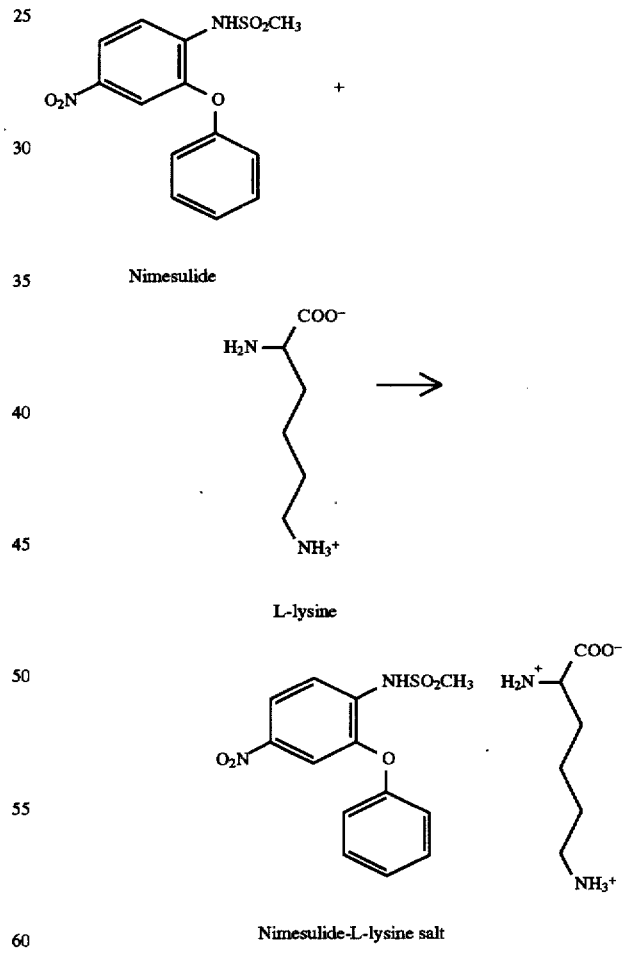

The operating conditions of the abovementioned reaction are the following. The nimesulide is dissolved with heating in methanol, preferably at a temperature close to the boiling point of methanol, advantageously at a temperature of 54° to 64° C. The L-lysine, for its part, is also dissolved in methanol, preferably also in methanol heated to a temperature of 54° to 64° C., but this is not compulsory. In fact, it would be possible to conceive the preparation of a methanolic solution of L-lysine at ambient temperature, which is then poured into the hot methanolic solution of nimesulide. Anyway, hot methanol makes it possible to dissolve both acidic nimesulide and L-lysine. Consequently, the reaction between the acid (nimesulide) and the base (L-lysine) is carried out by bringing into contact or mixing two solutions, giving a solution of the nimesulide-L-lysine salt which, after concentration and standing at low temperature, allows the expected salt to crystallize. The latter, collected on a filter, can then be washed with methanol, which makes it possible to assume that the contaminants of the salt (unconverted excess acidic nimesulide or, conversely, unconverted excess lysine) will be removed by this washing with methanol, because they are relatively soluble in the latter.

Insofar as the duration of placing the two methanolic solutions in contact is concerned, this is extremely short because, in principle, an acid-base reaction is instantaneous.

In accordance with the invention it is also possible to improve substantially the solubility of the nimesulide-L-lysine salt in water by combining it with L-arginine. Particularly satisfactory results are obtained when aqueous solutions of nimesulide-L-lysine salt are employed in which the weight ratio of the nimesulide salt to L-arginine is of the order of 1/1.

The simultaneous use of L-lysine and of cyclodextrins makes it possible, in accordance with the invention, to increase the solubility of nimesulide to a maximum value higher than 20 mg/ml (value determined by a solubility diagram), that is more than 2,000 times the solubility of nimesulide. The nimesulide-based combinations of the invention consist of mixtures or complexes of nimesulide, of L-lysine and of cyclodextrin. It is thus that they can be in the form of a mixture of nimesulide, L-lysine and cyclodextrin, of a mixture of nimesulide-L-lysine salt and of cyclodextrin, of a nimesulide-cyclodextrin complex mixed with L-lysine or else of a nimesulide-L-lysine-cyclodextrin complex.

The cyclodextrins employed will be advantageously α-, β- and γ-cyclodextrins, their hydrates, their derivatives like alkylated and hydroxyalkylated cyclodextrin derivatives and their mixtures. The nimesulide-L-lysine-cyclodextrin molar ratio advantageously varies between 1/1/1 and 1/2/1.

These nimesulide-based combinations are prepared in aqueous solution and are obtained in the solid form by concentration of the solution at reduced pressure or else by any other technique such as freeze-drying or nebulization.

Examples of preparation of the nimesulide-L-lysine salt and of aqueous solution employing the nimesulide-L-lysine salt in combination with L-arginine and of nimesulide-L-lysine-cyclodextrin combinations in the form of complexes or of simple mixtures are given below.

EXAMPLE 1

Preparation of the nimesulide-L-lysine salt

Nimesulide (3.08 g; 0.01 mole) is dissolved in hot methanol (100 ml) maintained at 60° C. and then a methanolic solution (50 ml) of L-lysine "hydrate" (Janssen Chimica; 1.64 g; 0.01 mole calculated on lysine monohydrate) is added to it. The orangy solution obtained is optionally filtered hot to remove a slight remaining cloudiness. The clear methanolic filtrate is concentrated in a rotary evaporator to a volume of 80 ml. The salt suspension obtained is cooled to a temperature of +4° C. for 2 hours. The precipitate is collected on a sintered glass filter, washed twice with a small volume of methanol and dried (yield of ±3 g). The orangy filtrate to which diethyl ether (150 ml) has been added and which is cooled to a temperature of −30° C. for two days leaves a second crop of less pure salt.

Melting point of the nimesulide salt prepared in methanolic solution: 200–204° C. with decomposition. M.p. of the second crop precipitated from ether: 188–201° C. with decomposition.

Elemental analysis theoretical analysis
N: 12.33
C: 50.21
H: 5.77
S: 7.05
salt (methanol):
N: 12.43
C: 50.07
H: 5.88
S: 6.80
salt (ether)
N: 12.65
C: 50.11
H: 6.18
S: 6.35

The IR and NMR spectra confirm that the nimesulide-L-lysine salt is actually a new compound with physicochemical properties which differ from those of a physical mixture of equal parts of nimesulide and of L-lysine.

IR spectra

FIG. 1: spectrum of nimesulide

Figure 2:
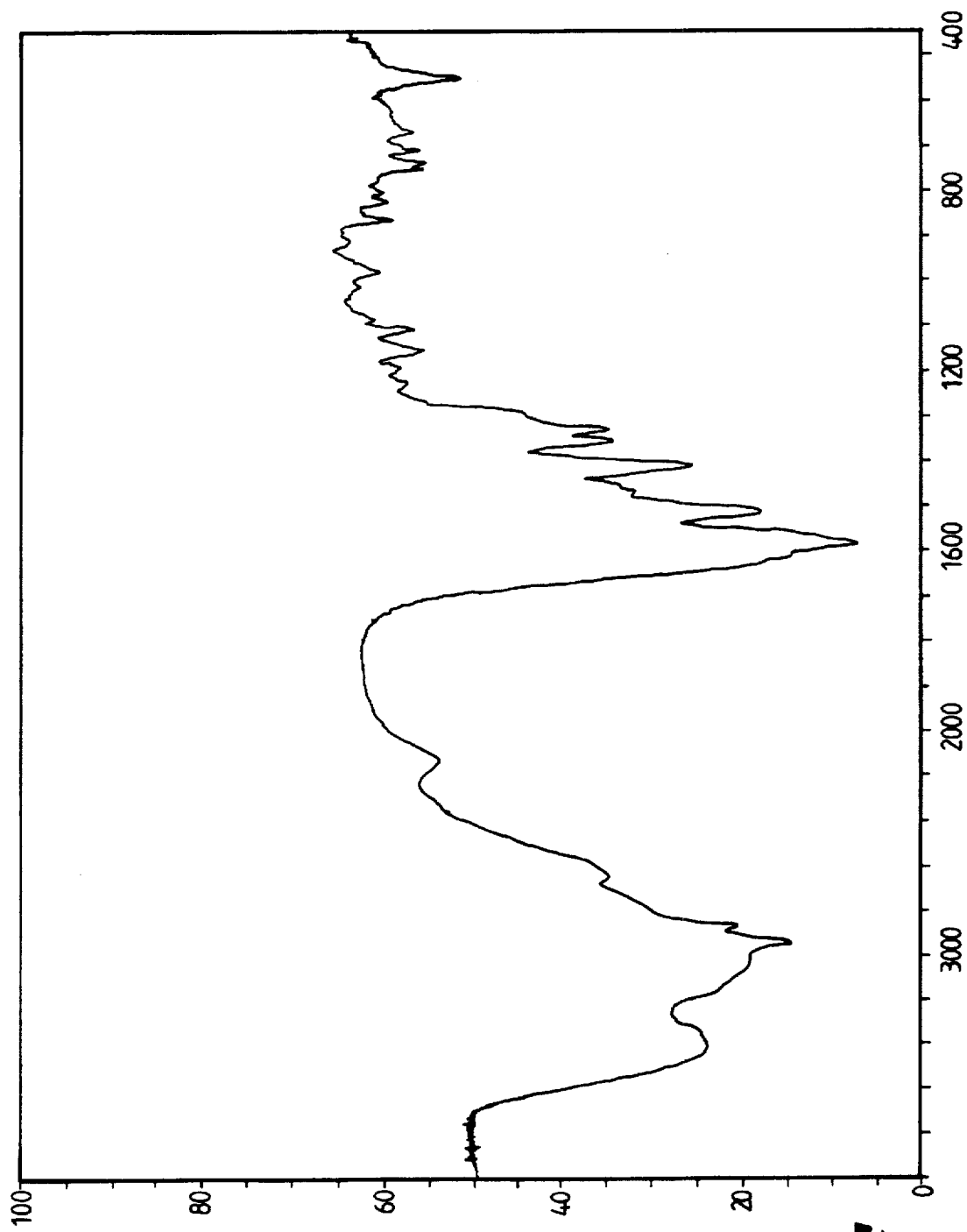

FIG. 2: spectrum of anhydrous L-lysine

Figure 3:
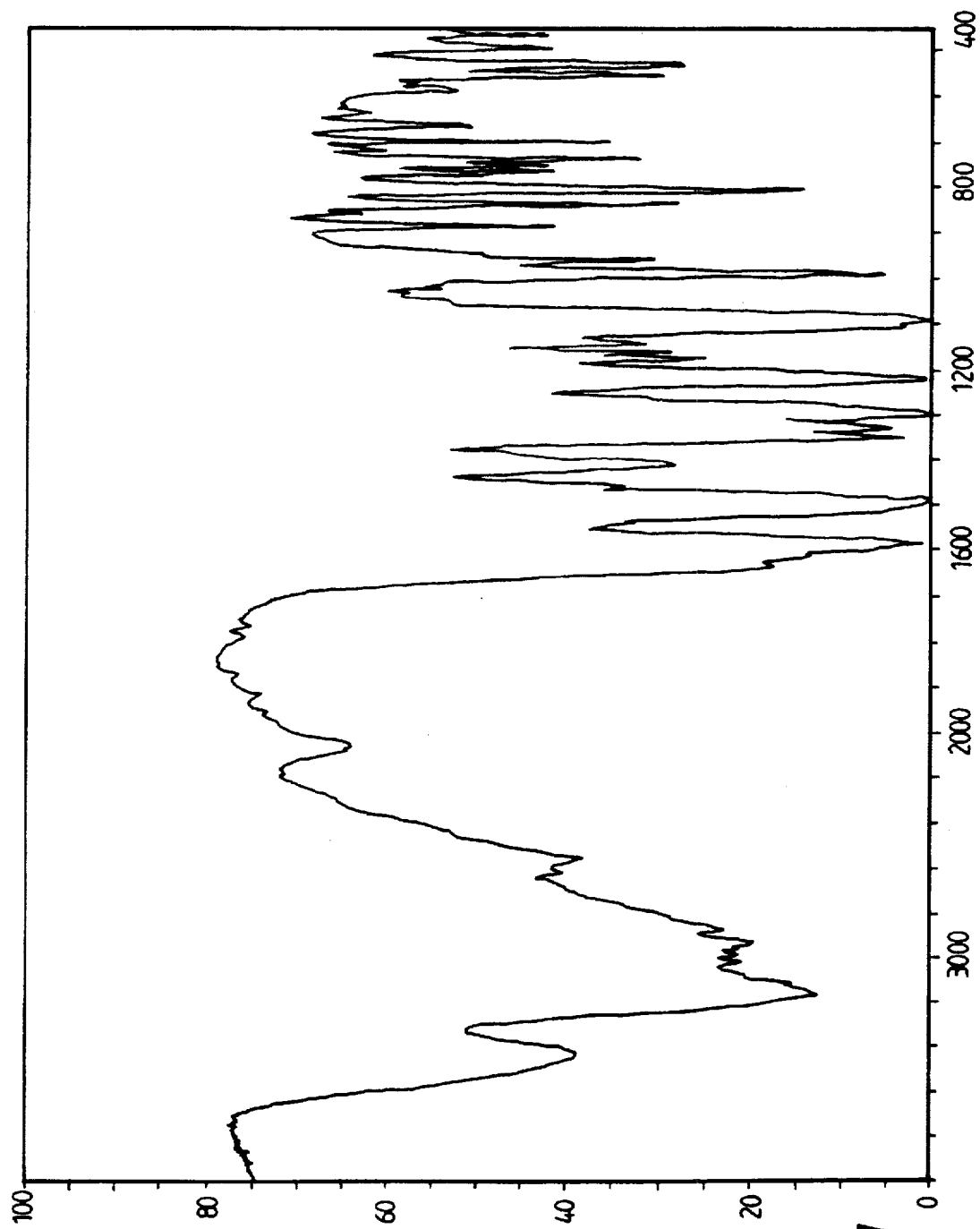

FIG. 3: spectrum of the nimesulide-L-lysine salt of the invention

Figure 4:
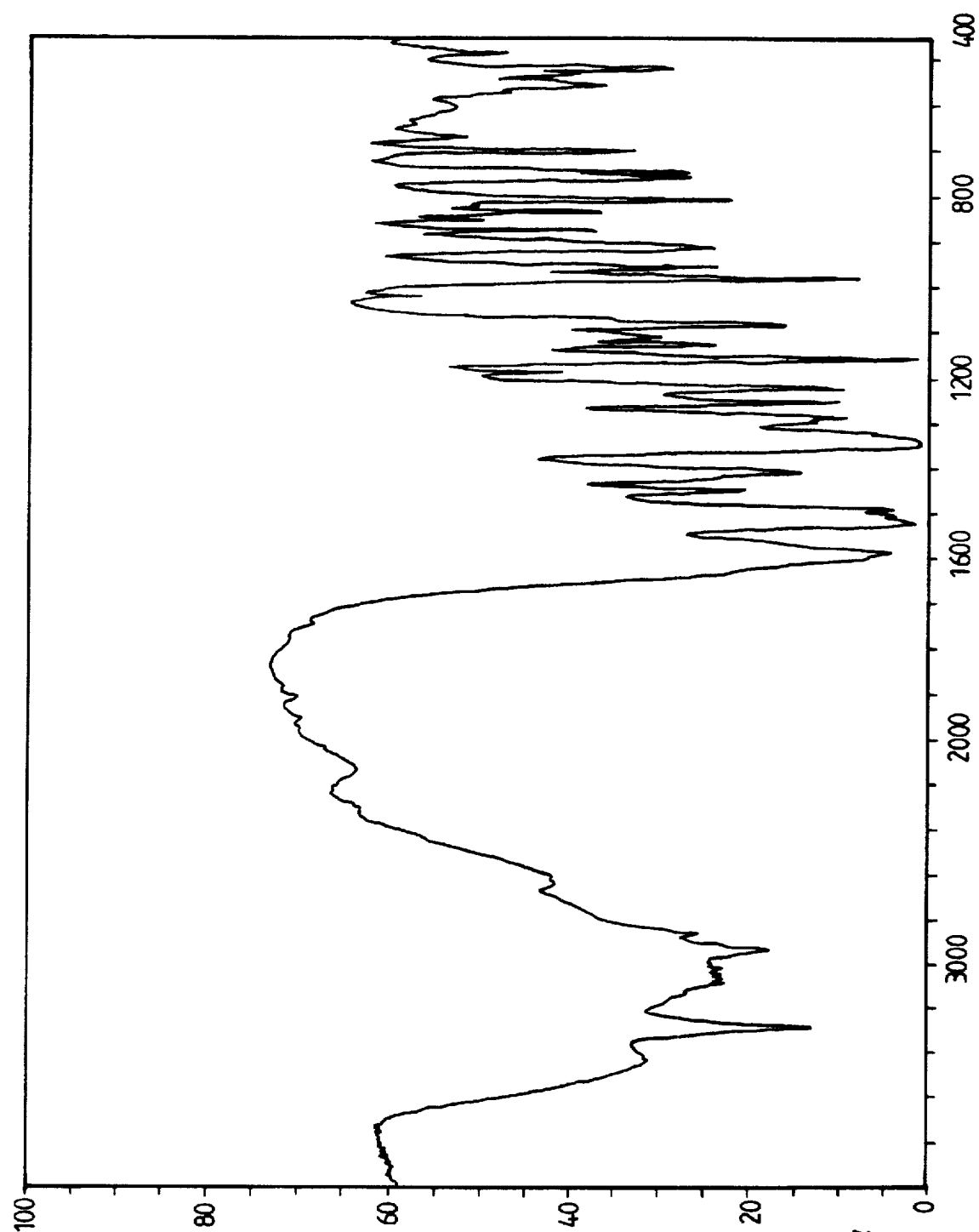

FIG. 4: spectrum of a physical mixture of nimesulide and of L-lysine

Figure 5:
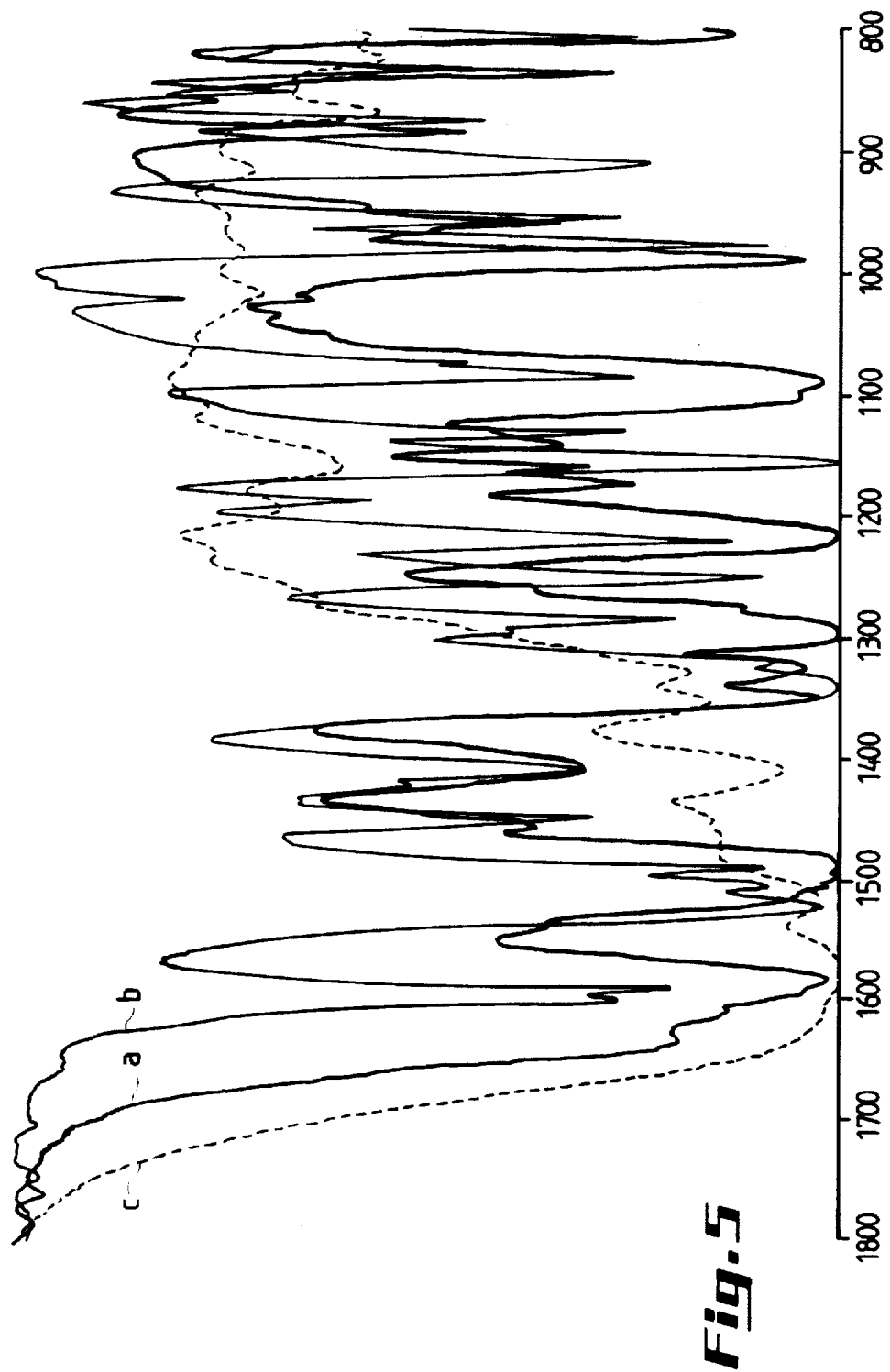

FIG. 5: superposition of the spectra of FIGS. 1, 2 and 3 between 800 and 1800 $cm^{-1}$.

It is seen in particular that the N-H stretching absorption band at 3284 $cm^{-1}$ present in the spectrum of FIG. 1 of nimesulide (therefore relating to the —$SO_2NH$— fragment involved in the salt formation) is not encountered again in the spectrum of FIG. 3 of the salt (since, in principle, this fragment becomes —$SO_2N^{(-)}$ in the salt structure), but is seen in the spectrum of FIG. 4 of the physical mixture of the partners.

Furthermore, the spectrum of FIG. 5, which displays the superposition of the spectra of FIGS. 1, 2 and 3 between 800 and 1800 $cm^{-1}$, shows that the salt (a) exhibits absorption bands which are different from those of the acidic nimesulide (b) and of lysine (c). In particular, to mention only these, the clear absorption bands at about 900 $cm^{-1}$, at about 1150 $cm^{-1}$ and at about 1250 $cm^{-1}$ of the acidic nimesulide have disappeared in the spectrum of the salt.

It can therefore be concluded that a number of new bonds with IR absorption characteristics have been formed in the salt, probably giving evidence of the deprotonation of the —$SO_2NH$— functional group in nimesulide.

NMR spectra

Figure 6:
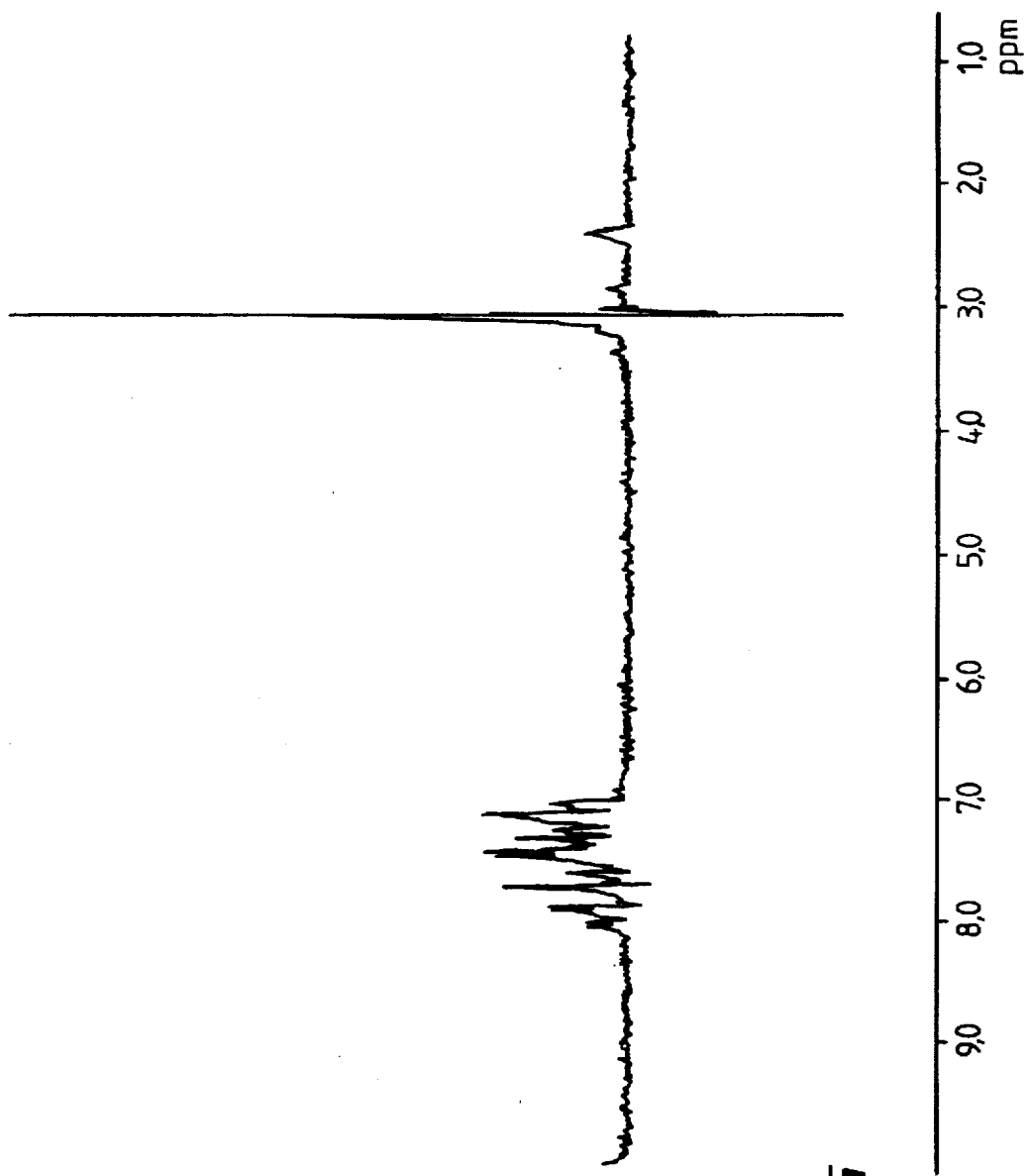

FIG. 6: spectrum of acidic nimesulide in deuterated DMSO (+HMDS) between 0 and 10 ppm.

Figure 7:
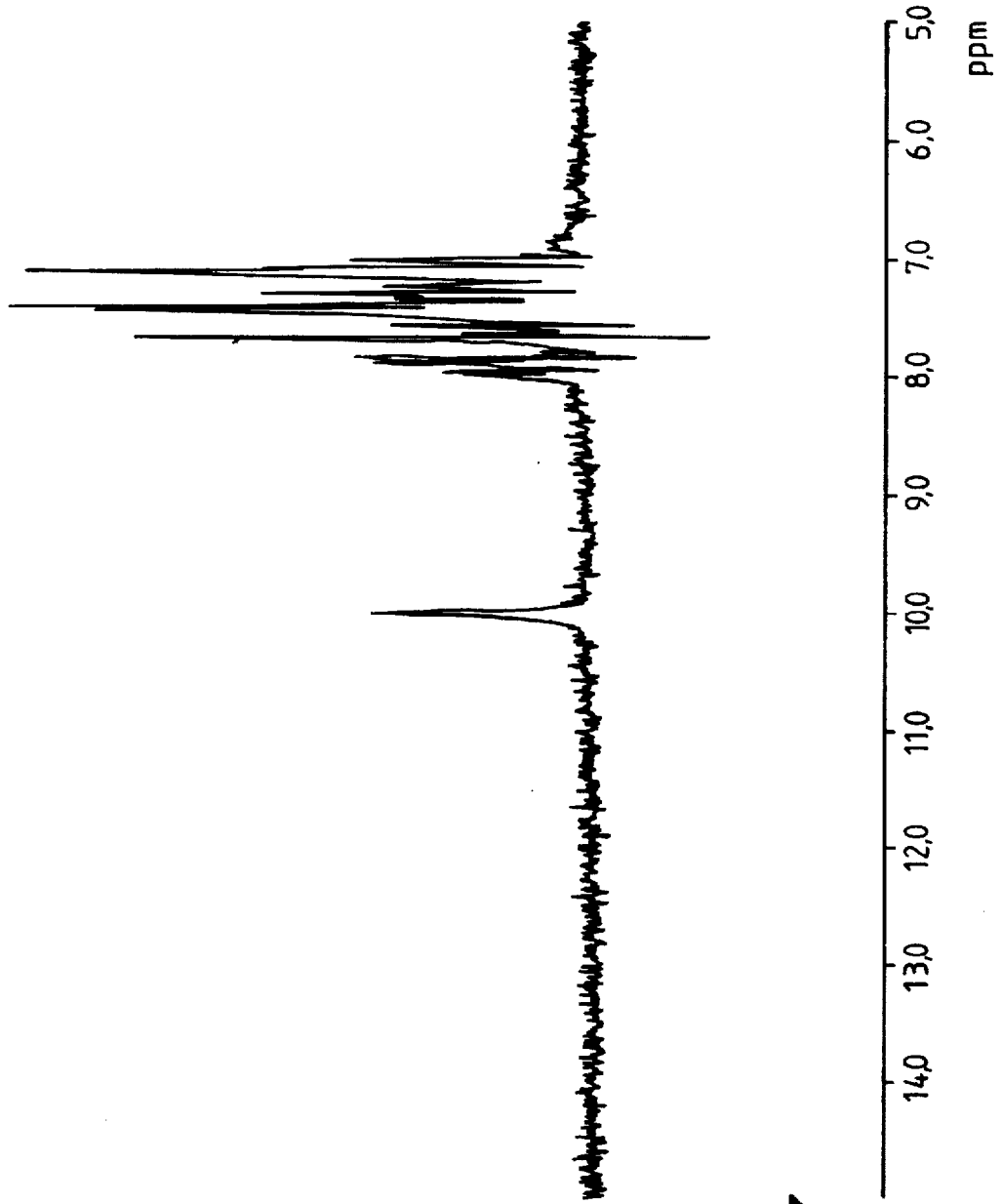

FIG. 7: spectrum of acidic nimesulide in deuterated DMSO (+HMDS) between 5 and 15 ppm.

Figure 8:
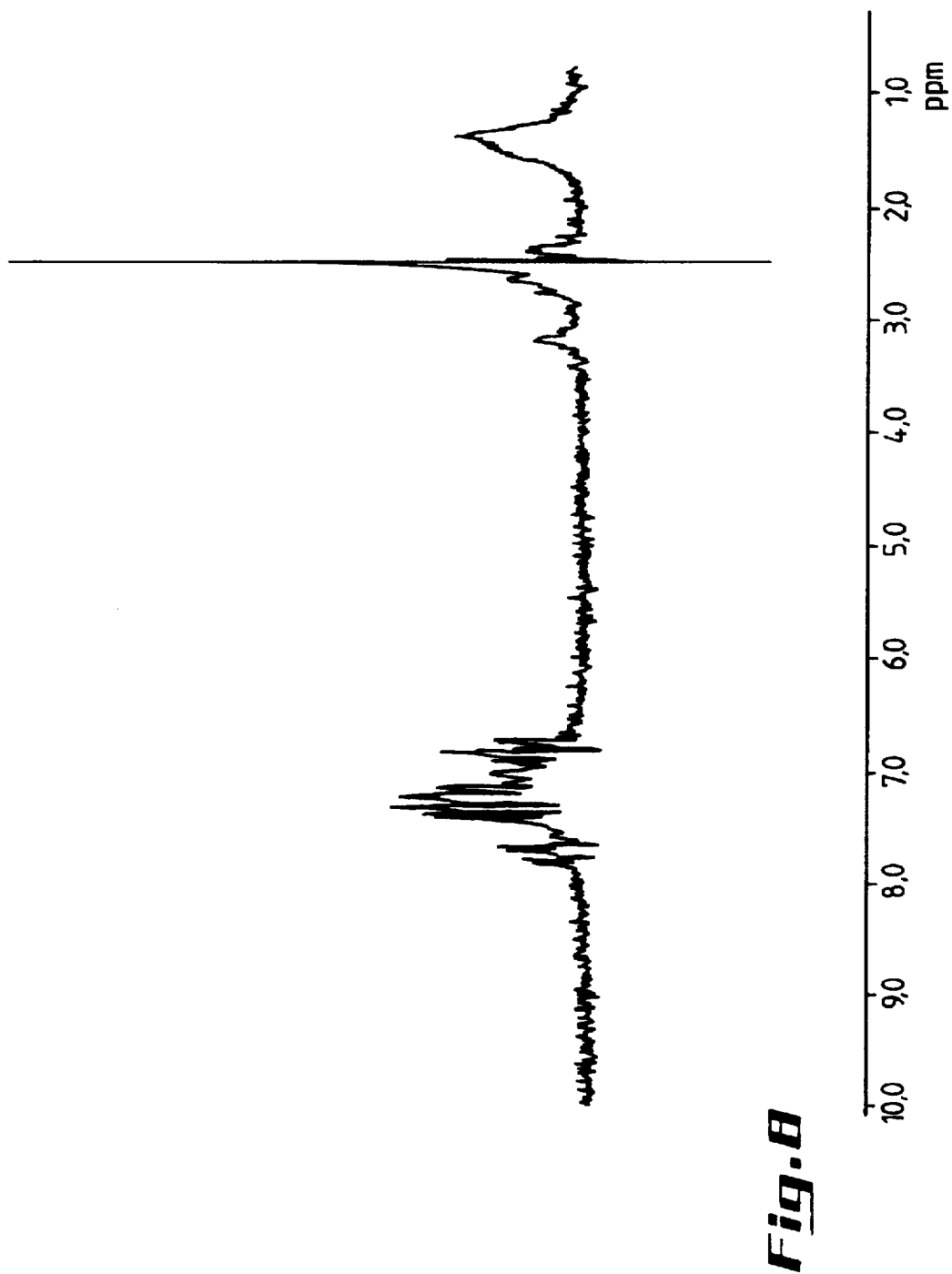

FIG. 8: spectrum of the salt of nimesulide with L-lysine in deuterated DMSO (+HMDS) between 0 and 10 ppm.

Figure 9:
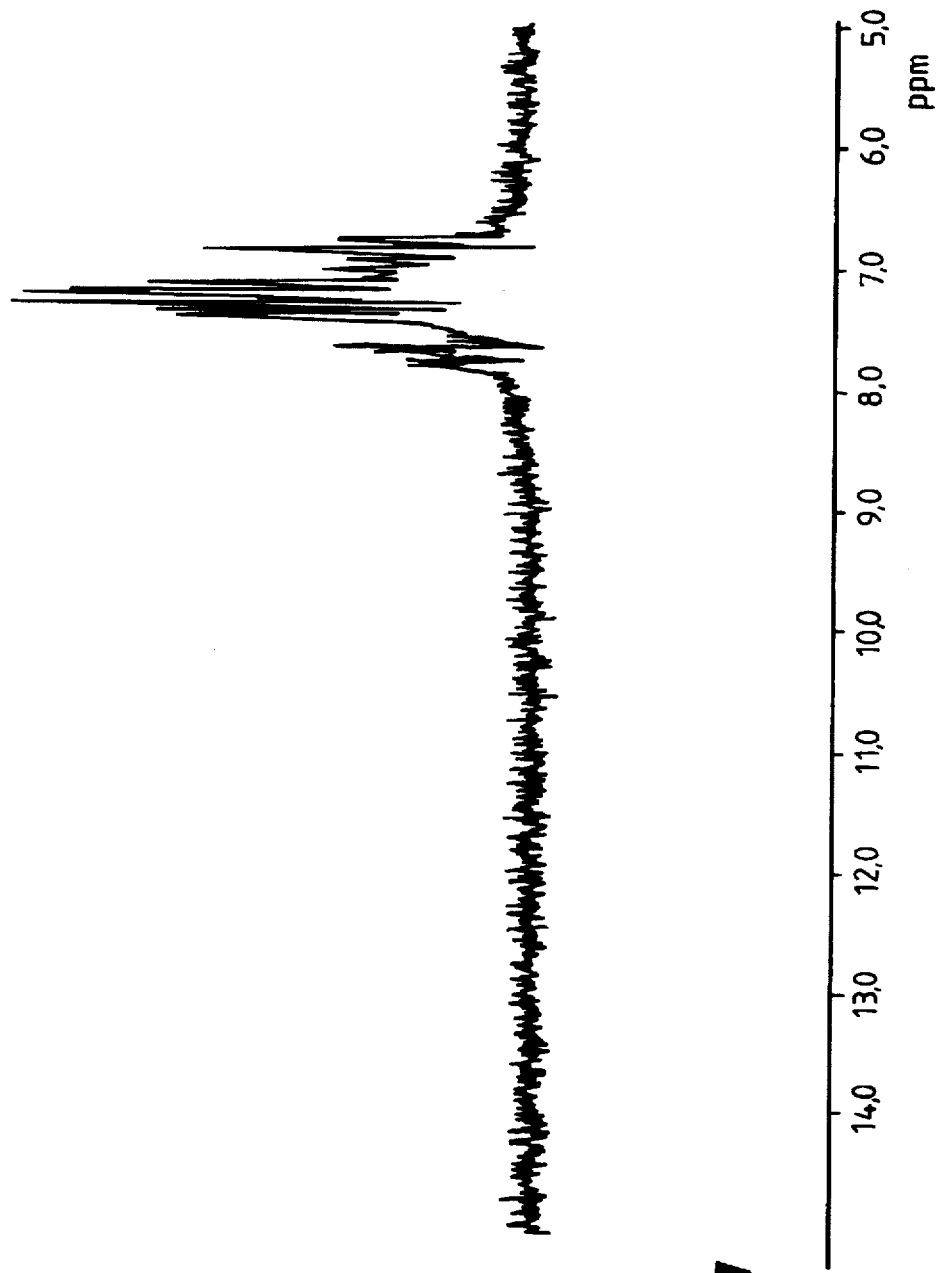

FIG. 9: spectrum of the salt of nimesulide with L-lysine in deuterated DMSO (+HMDS) between 5 and 15 ppm.

The spectrum in FIG. 7 shows the presence, in the case of acidic nimesulide, of a strongly deshielded (acidic) proton corresponding to the proton of the —$SO_2NH$— functional group.

When compared with the spectrum in FIG. 7, the spectrum in FIG. 9 of the salt shows the disappearance of the —$SO_2NH^{(-)}$ proton signal at about 10 ppm.

On the other hand, when compared with the spectrum in FIG. 6, the spectrum of FIG. 7 shows the additional signals corresponding to the C—H protons of lysine.

It is also seen that the formation of the nimesulide salt with lysine gives rise to an $SO_2N^{(-)}$functional group which, bearing in mind the increase in the electron density related to the negative charge, induces a generalized shielding of the protons in the nimesulide part. In particular, the three methyl protons present in the spectrum in FIG. 6 at about 3.0 ppm in the case of the acid are found to be shifted towards 2.5 ppm in the case of the salt.

EXAMPLE 2

Preparation of an aqueous solution of nimesulide-L-lysine salt with addition of L-arginine To carry out the dissolving of 10 mg of nimesulide per milliliter of aqueous solution, the nimesulide-L-lysine salt as prepared in Example 1 (15 mg) is employed, to which 15 mg of L-arginine have been added. This combination of the nimesulide-L-lysine salt with L-arginine enables the solubility of the salt in water to be appreciably increased. It will be noted in this context that the nimesulide-L-lysine salt dissolved in water partially salts out some insoluble acidic nimesulide.

The water-soluble nimesulide-L-lysine salt of the present invention exerts a remarkable antiinflammatory activity in all the inflammatory disorders in which acidic nimesulide is employed. Thus, the salt of the invention can be used for the preparation of drinkable or injectable solutions of nimesulide by means of a suitable formulation, for example with the addition of L-arginine. It will be noted in this context that known nimesulide salts (sodium salt or amine salts) in solution impose a relatively alkaline pH of which it is necessary to be aware when they are formulated in an injectable form. On the other hand, the nimesulide-L-lysine salt, whether or not linked with L-arginine, imposes a markedly less alkaline pH in solution than the alkali metal salts and this, as is known, constitutes a very considerable advantage when compared with the latter.

The water-soluble nimesulide-L-lysine salt of the invention can be administered in combination with various pharmaceutical excipients, such as diluents, gelling agents, preserving agents, emulsifiers, sweeteners and flavors, this being by oral, parenteral or rectal route.

For an oral administration, sugar-coated tablets, granulates, lozenges, tablets, capsules, pills, solutions, syrups and emulsions containing additives or excipients which are conventional in galenic pharmacy will be employed. These galenic forms may release the principle in a normal or programmed manner in time.

For parenteral administration any suitable carrier will be employed, like, for example, sterile water.

For rectal administration, suppositories, rectal capsules, solutions or gels will be employed.

The active compound may be administered by itself or in combination with other active products which have a similar or different activity.

The following example demonstrates the part played by β and γ-cyclodextrins (β-CD and γ-CD) in the solubility of the nimesulide-L-lysine salt.

EXAMPLE 3

Solubility diagram of the nimesulide-L-lysine salt as a function of the quantity of β- and γ-CD An excess of nimesulide-L-lysine salt is suspended in 20 ml of water containing increasing concentrations of β- or γ-CD (0, 10, 20, 30, 40, 50, 100, 200 and 300 mM). The whole is agitated at 20° C. for 10 days. The mixtures are then filtered through a 0.45 μm membrane. The dissolved nimesulide is determined by spectrophotometry at 397 nm after appropriate dilution in a 0.1N NaOH solution.

Table 1 below summarizes the results obtained:

TABLE 1

| Concentration of β- or γ-CD | Nimesulide dissolved in presence of β-CD | | Nimesulide dissolved in presence of γ-CD | |
|---|---|---|---|---|
| (mM) | mg/ml | mM | mg/ml | mM |
| 0 | 5.42 | 17.60 | 5.42 | 17.60 |
| 10 | 6.97 | 22.60 | 8.75 | 28.40 |
| 20 | 8.60 | 27.90 | 12.00 | 38.90 |
| 30 | 10.41 | 33.80 | 15.22 | 49.40 |
| 40 | 11.77 | 38.20 | 17.68 | 57.30 |
| 50 | 16.32 | 52.90 | 23.63 | 76.60 |
| 100 | 25.31 | 82.10 | 30.27 | 98.20 |
| 200 | 25.23 | 81.80 | 30.16 | 97.80 |

Figure 10:
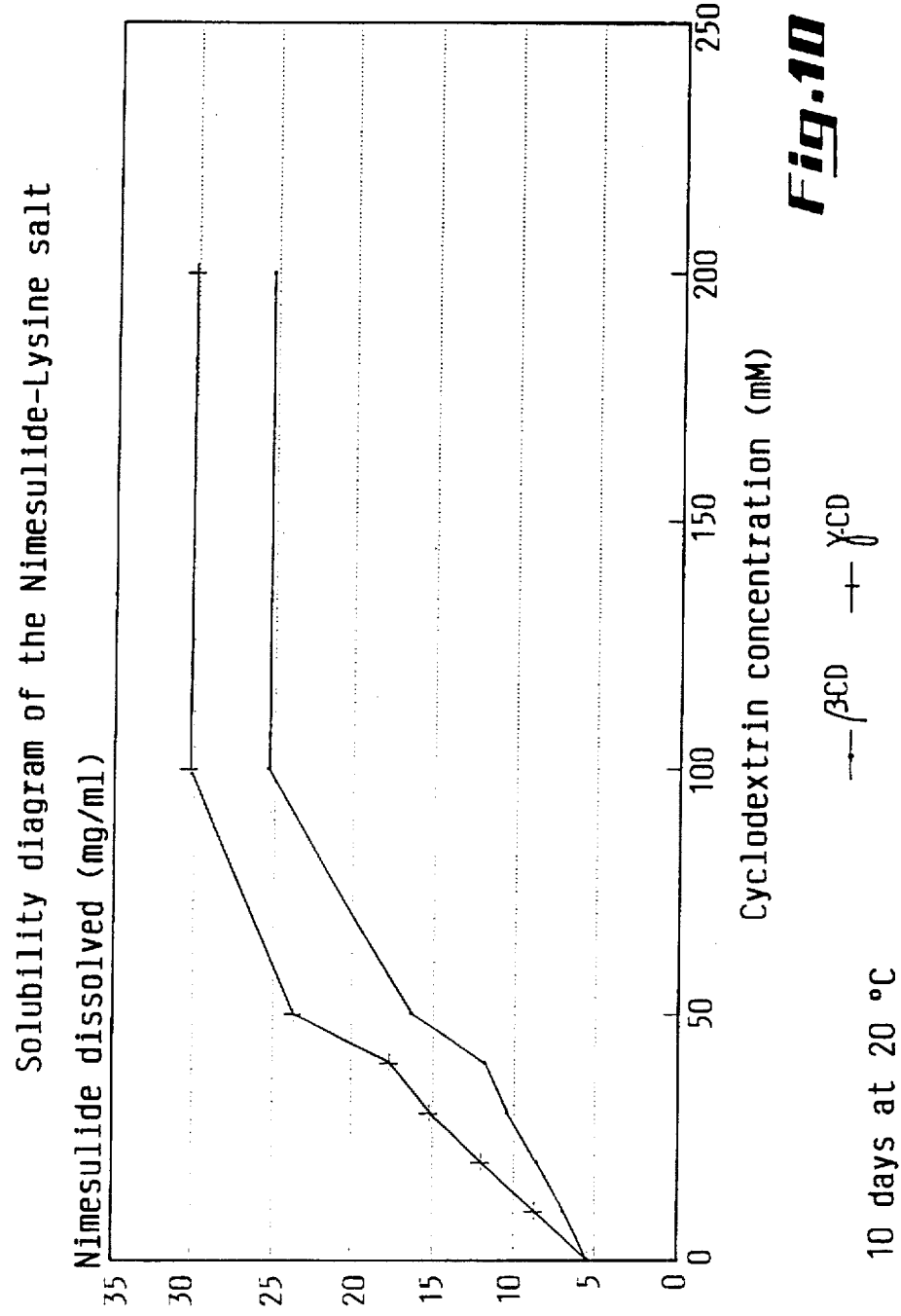

These results are shown in FIG. 10.

EXAMPLE 4

Preparation of the nimesulide-L-lysine-β-CD combination in the molecular ratio 1/1/1

2.63 g of β-CD.10H$_2$O (2×10$^{-3}$ mole) and 0.62 g of nimesulide (2×10$^{-3}$ mole) are suspended in 40 ml of water and brought to 85°–90° C. with agitation. L-lysine monohydrate is added in small portions to the suspension until completely dissolved (0.48–0.50 g of L-lysine: 2.9–3×10$^{-3}$ mole). The solution is concentrated in the rotary evaporator until a translucent viscous liquid is obtained (±8 ml). The latter is left at ambient temperature for 24 hours. A crystalline precipitate appears slowly. The next day the precipitate is collected on a filter, washed with a minimum of distilled water and dried. ±1.27 g of a crystalline yellow product are collected.

The nimesulide-L-lysine-β-CD combination can be obtained from the nimesulide-L-lysine salt and from β-CD by progressively adding L-lysine monohydrate until a suspension heated to 85°–90° C. is completely dissolved. The same ratio of total molar fractions of β-CD, nimesulide and L-lysine which are introduced is obtained.

| Analyses of the compound obtained: | | |
|---|---|---|
| Nimesulide-L-lysine-β-CD.10H$_2$O combination | Theoretical content | Measured value |
| Elemental analysis: | | |
| % N | 3.17 | 3.57 |
| % C | 41.39 | 42.06 |
| % H | 6.61 | 7.15 |

-continued

| Analyses of the compound obtained: | | |
|---|---|---|
| Nimesulide-L-lysine-β-CD.10H$_2$O combination | Theoretical content | Measured value |
| % S | 1.81 | 1.67 |
| Water content (%)* | 10.17 | 10.40 |
| Nimesulide content (%)** | 17.42 | 17.51 |

*measured by the Karl Fisher [sic] method
**determined by visible spectrophotometry at 397 nm after appropriate dilution in 0.1N NaOH.

The elemental analyses (C, H, N, S) and the analyses for water and nimesulide content indicate that the solid compound obtained corresponds in practice to a combination of nimesulide-L-lysine salt and of β-CD in a 1/1/1 molecular ratio and combined with 10 molecules of water of crystallization. Hence, the excess of L-lysine employed is removed during the filtration of the solid.

EXAMPLE 5

Preparation of the nimesulide-L-lysine-β-CD inclusion complex by nebulization 6.16 g of nimesulide ($2 \times 10^{-2}$ mole) are suspended in 200 ml of distilled water to which 6.56 g of L-lysine ($4 \times 10^{-2}$ mole) are added. The suspension is subjected to ultrasound for 5 minutes and then heated to 50° C. while violent agitation is maintained [Ultraturrax (registered mark)]. 26.3 g of β-CD•10H$_2$O ($2 \times 10^{-2}$ mole) are dispersed in 200 ml of distilled water and heated to 50° C. The suspension of β-CD is added to the suspension of nimesulide and L-lysine. The agitation is continued for 15 minutes. An orangy solution is obtained.

This solution is nebulized (Niro Atomizer Mobile atomizer) in the following conditions:

Pressure: 2–3 bars
Entry temperature: 150°–160° C.
Exit temperature: 60°–70° C.
Throughput: ±25 ml/min
The yield is ±80%.

The product obtained is an odorless, bright yellow powder and therefore corresponds to a nimesulide-L-lysine-β-CD•8H$_2$O (1/2/1) complex or combination or more probably to a nimesulide-L-lysine-β-CD•8H$_2$O (1/1/1) complex with one molecular equivalent of excess L-lysine.

The elemental analysis gives the following values:

| % of | Theoretical value* | Measured value |
|---|---|---|
| C | 42.85 | 42.84 |
| H | 6.72 | 6.64 |
| N | 4.48 | 4.34 |
| S | 1.70 | 1.38 |

*For a nimesulide-L-lysine-β-CD.8H$_2$O (1/2/1) combination.

The isolated product exhibits the following characteristics:

Solubility in water: 350 mg/ml (60.7 mg of nimesulide/ml)
Solubility in 0.1N HCl: 48.02 µg of nimesulide/ml
Solubility at pH 6.8: 2.37 mg of nimesulide/ml
pH of a 2% solution: 8.85–8.95
Water content: 7.6%
Nimesulide content: 15.67%.

Figure 11:
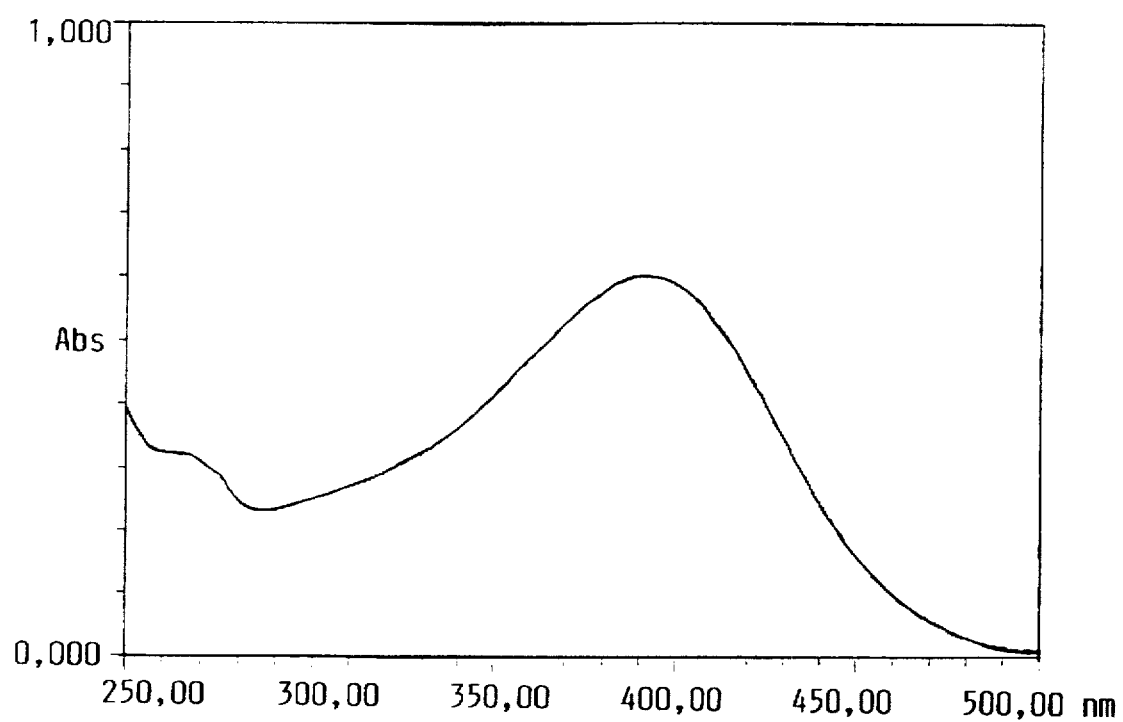

The UV spectrum between 250 and 500 nm (FIG. 11) shows that all the nimesulide is in ionized form (nimesulide-L-lysine) because there is no absorption maximum at 297 nm corresponding to the absorption maximum of acidic nimesulide.

Figure 12:
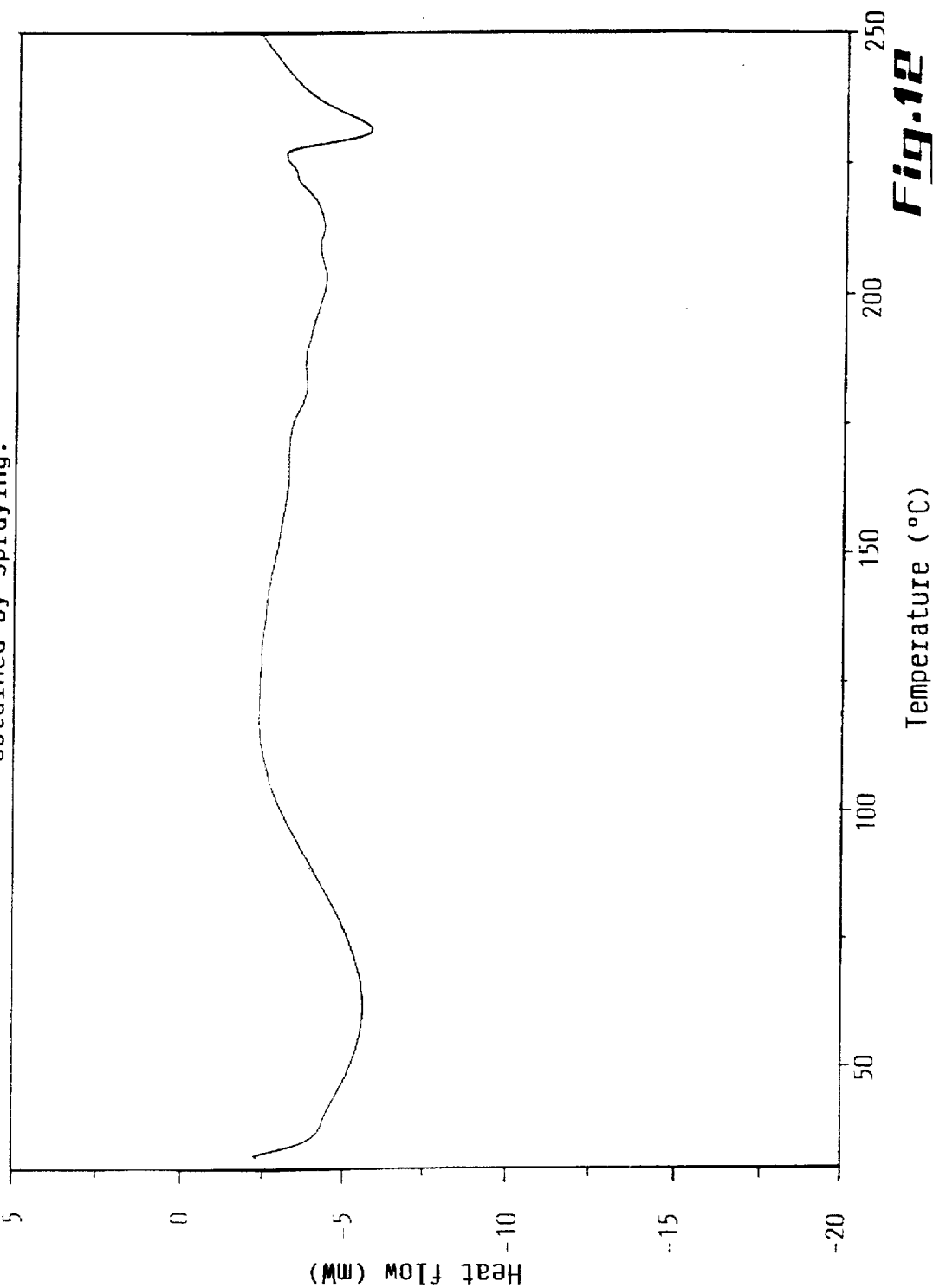
Figure 13:
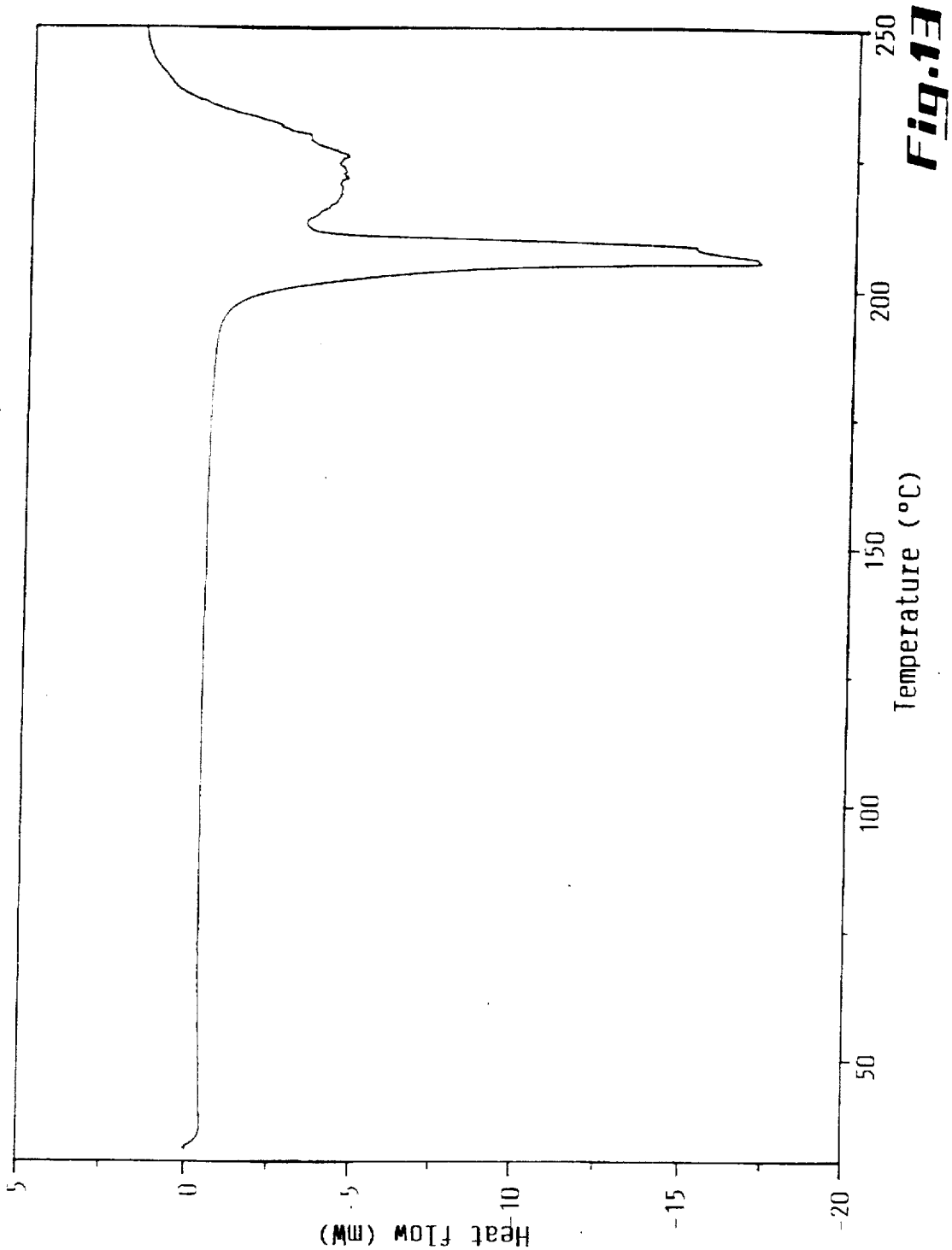
Figure 14:
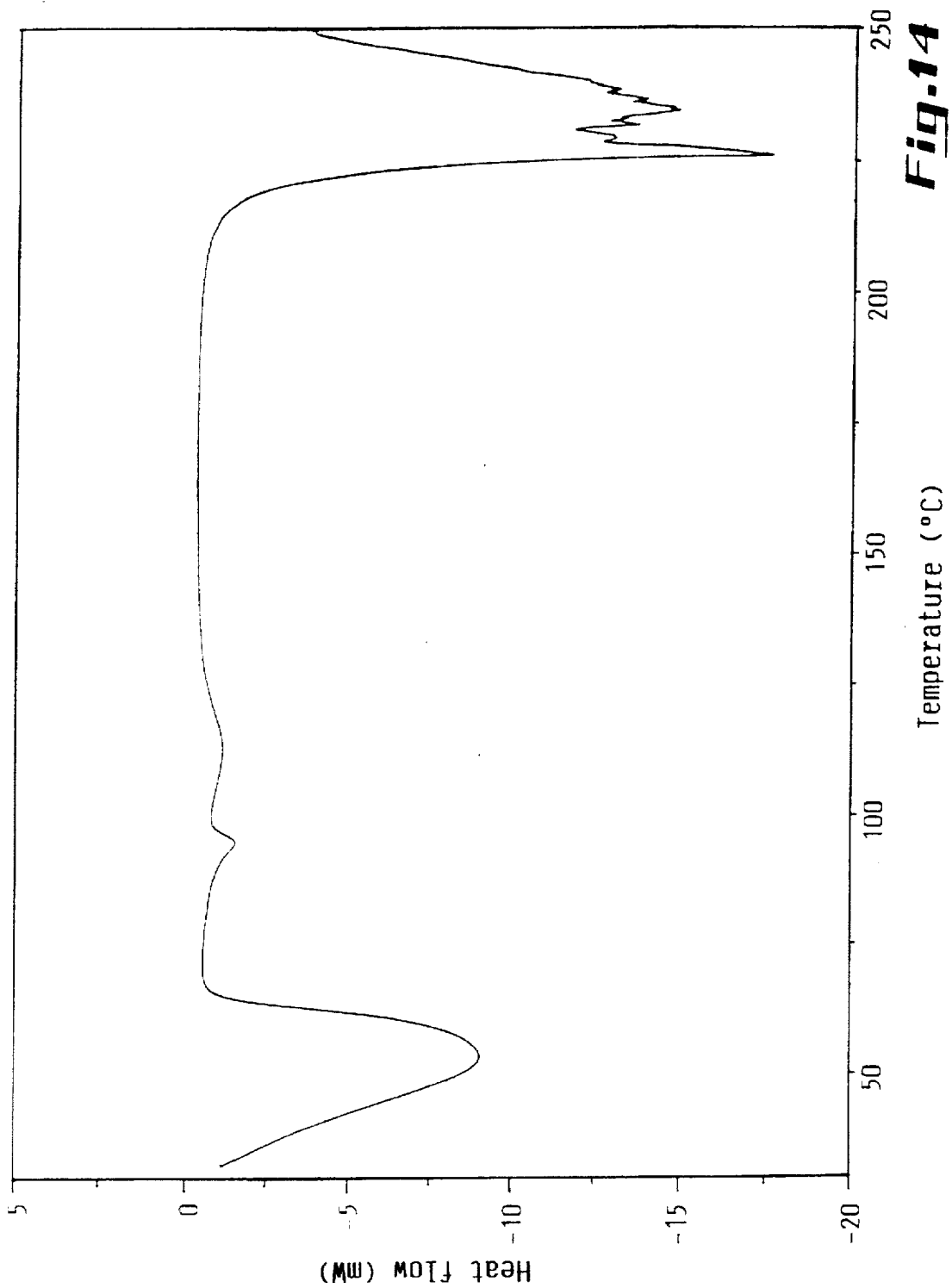
Figure 15:
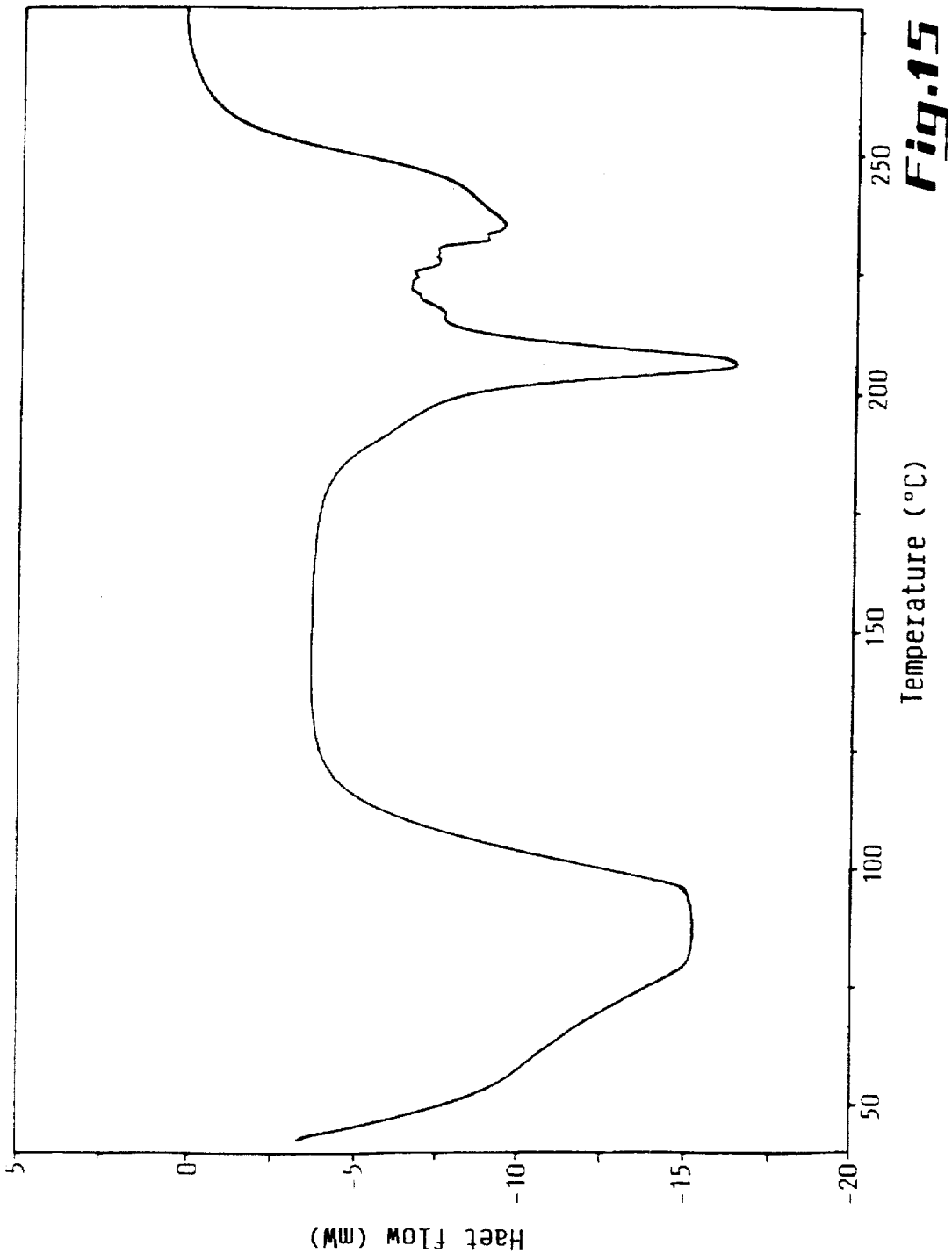

Proofs of inclusion:

Differential thermal analyses (DTA): FIG. 12 shows the differential thermal analysis (DTA) thermogram of the product obtained by nebulization. The DTA thermogram of the nimesulide-L-lysine salt (FIG. 13) shows a melting endotherm at about 208° C., L-lysine (FIG. 14) shows chiefly an endotherm at about 225° C. A physical mixture of nimesulide-L-lysine salt+L-lysine+β-CD produced so as to obtain the same molecular fractions as the nebulized products (FIG. 15) enables the characteristic endotherm of the salt and of L-lysine to be found again.

The endotherm before 100° C. corresponds to the water loss. It will be noted that the complex (FIG. 12) no longer exhibits the characteristic endotherm of the nimesulide-L-lysine salt, which tends to prove the inclusion, in the solid state, of the nimesulide-L-lysine salt in β-CD. On the other hand, an excess of L-lysine at about 225° C. and the water loss before 100° C. are found again.

EXAMPLE 6

Preparation of the nimesulide-L-lysine-γ-CD inclusion complex by nebulization 3 g of nimesulide ($9.73 \times 10^{-3}$ mole) are suspended in 200 ml of distilled water to which 3.2 g of L-lysine ($1.95 \times 10^{-2}$ mole) are added. The suspension is subjected to ultrasound for 5 minutes and then heated to 50° C. while violent agitation is maintained [Ultraturrax (registered mark)]. 13.88 g of γ-CD•7H$_2$O ($9.73 \times 10^{-3}$ mole) are dispersed in 200 ml of distilled water and heated to 50° C. The suspension of γ-CD is added to the suspension of nimesulide+L-lysine. The agitation is continued for 15 minutes. An orangy solution is obtained. This solution is nebulized (Niro Atomizer Mobile atomizer) in the following conditions:

Pressure: 2–3 bars
Entry temperature: 150°–160° C.
Exit temperature: 60°–70° C.
Throughput: ±25 ml/min
The yield is ±80%.

The product obtained is an odorless, bright yellow powder and exhibits the following characteristics:

Solubility in water: 300 mg/ml (47.67 mg of nimesulide/ml)
Solubility in 0.1N HCl: 20.28 µg of nimesulide/ml
Solubility at pH 6.8: 1.71 mg of nimesulide/ml
pH of a 2% solution: 8.98
Water content: 5.98%
Nimesulide content: 14.94%.

Figure 16:
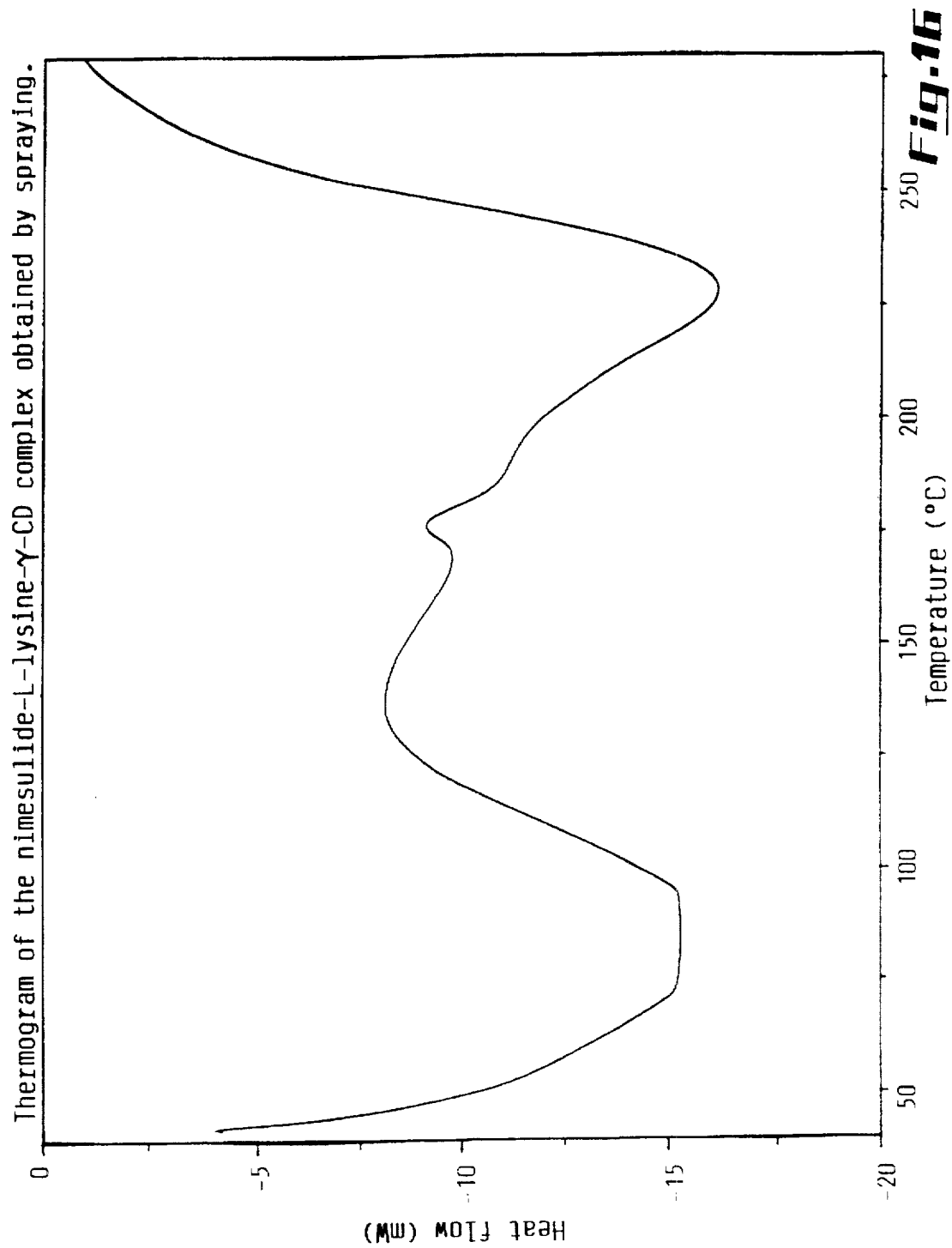
Figure 17:
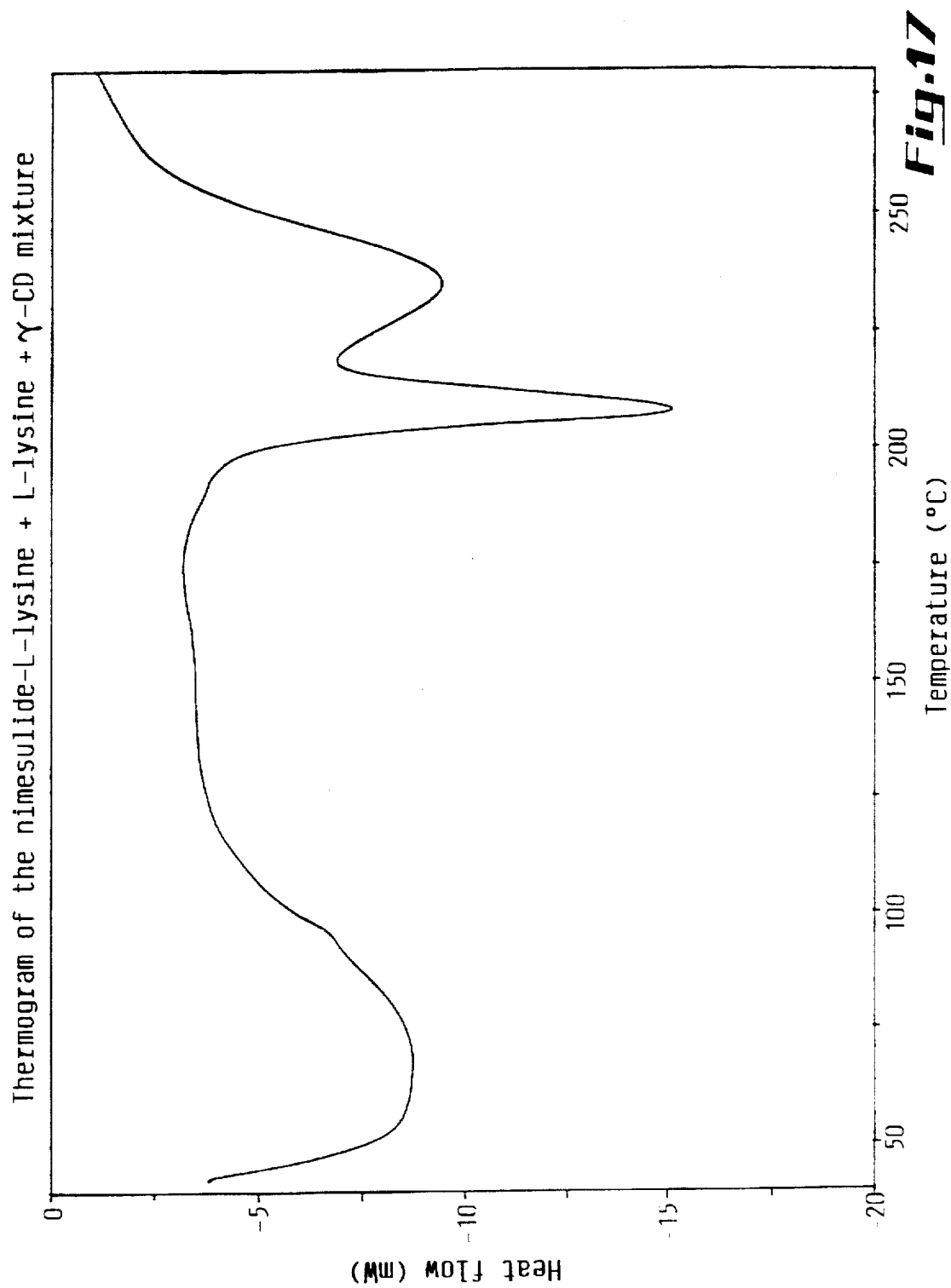

Proofs of inclusion:

Differential thermal analyses (DTA): FIG. 16 shows the differential thermal analysis (DTA) thermogram of the complex and FIG. 17 shows the differential thermal analysis (DTA) thermogram of a nimesulide-L-lysine+L-lysine+γ-CD mixture. In the case of the complex the water loss below 100° C. and the excess of L-lysine at ±227° C. are found again, but no endotherm at about 208° C. corresponding to the nimesulide-L-lysine salt. The inclusion is demonstrated by this technique in the solid state.

DTA shows that nimesulide in the form of nimesulide-L-lysine salt is practically completely included in β- and γ-CD in the form of an inclusion complex and that the solid combination isolated by nebulization is the combination of this inclusion complex with an excess of L-lysine.

EXAMPLE 7

Proof of inclusion in β-CD in solution by $^1$H NMR

A study using 80 MHz and 400 MHz $^1$H NMR in $D_2O$ was carried out in order to prove the possible existence of an inclusion in aqueous solution. The dissolving of the nimesulide L-lysine salt and the nimesulide-L-lysine-β-CD (1/1/1) combination was performed in the presence of an excess of L-lysine (two equivalents of L-lysine per one equivalent of nimesulide) in order to avoid any risk of release of a small quantity of acidic nimesulide which is very poorly soluble in water, and to remain in the same stoichiometric proportions as the complexes prepared by nebulization. The spectra were recorded between 0 and 10 ppm.

Figure 18:
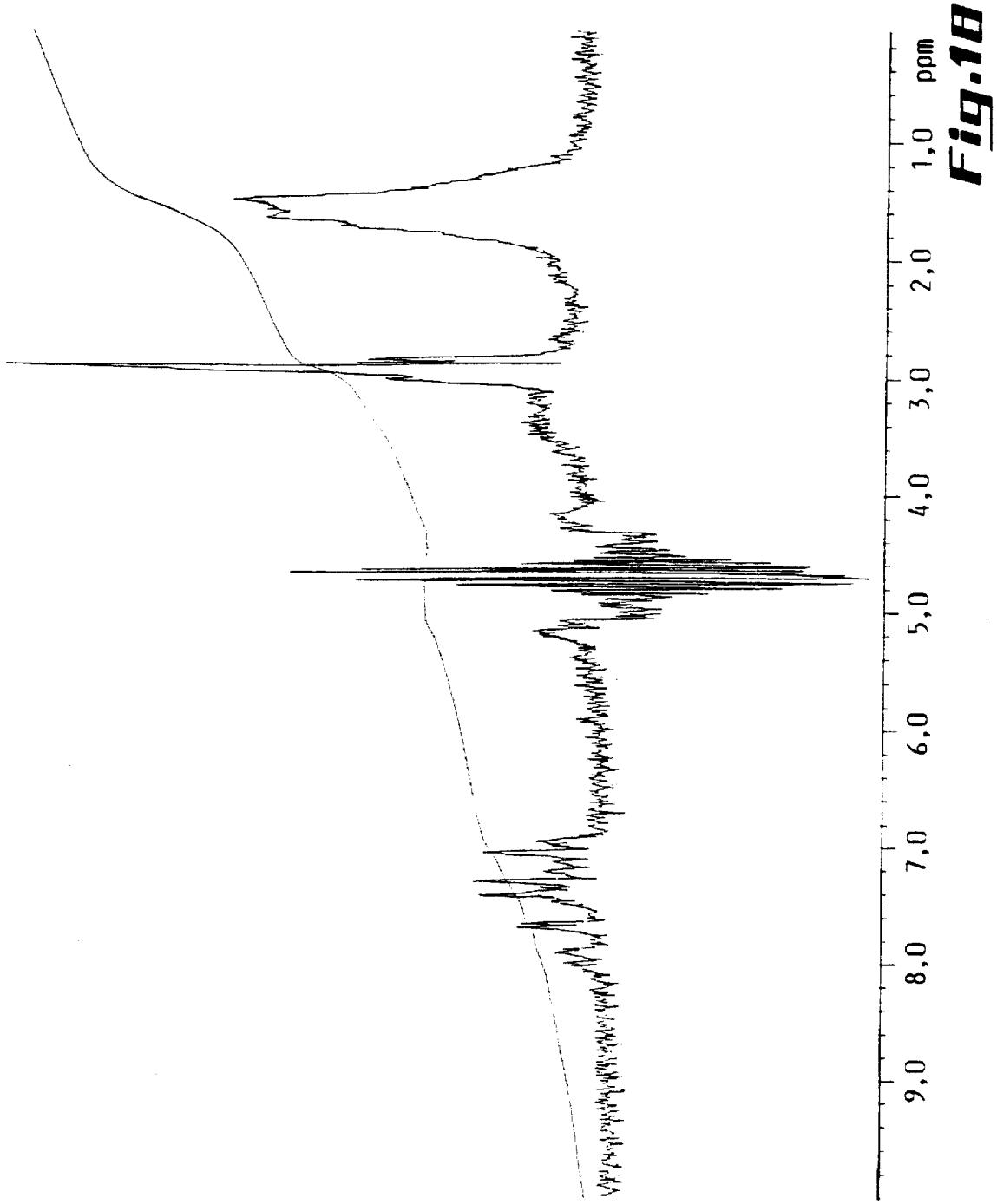

FIG. 18: 80 MHz $^1$H NMR spectrum of the nimesulide L-lysine salt in $D_2O$ between 0 and 10 ppm, in the presence of an excess of L-lysine.

Figure 19:
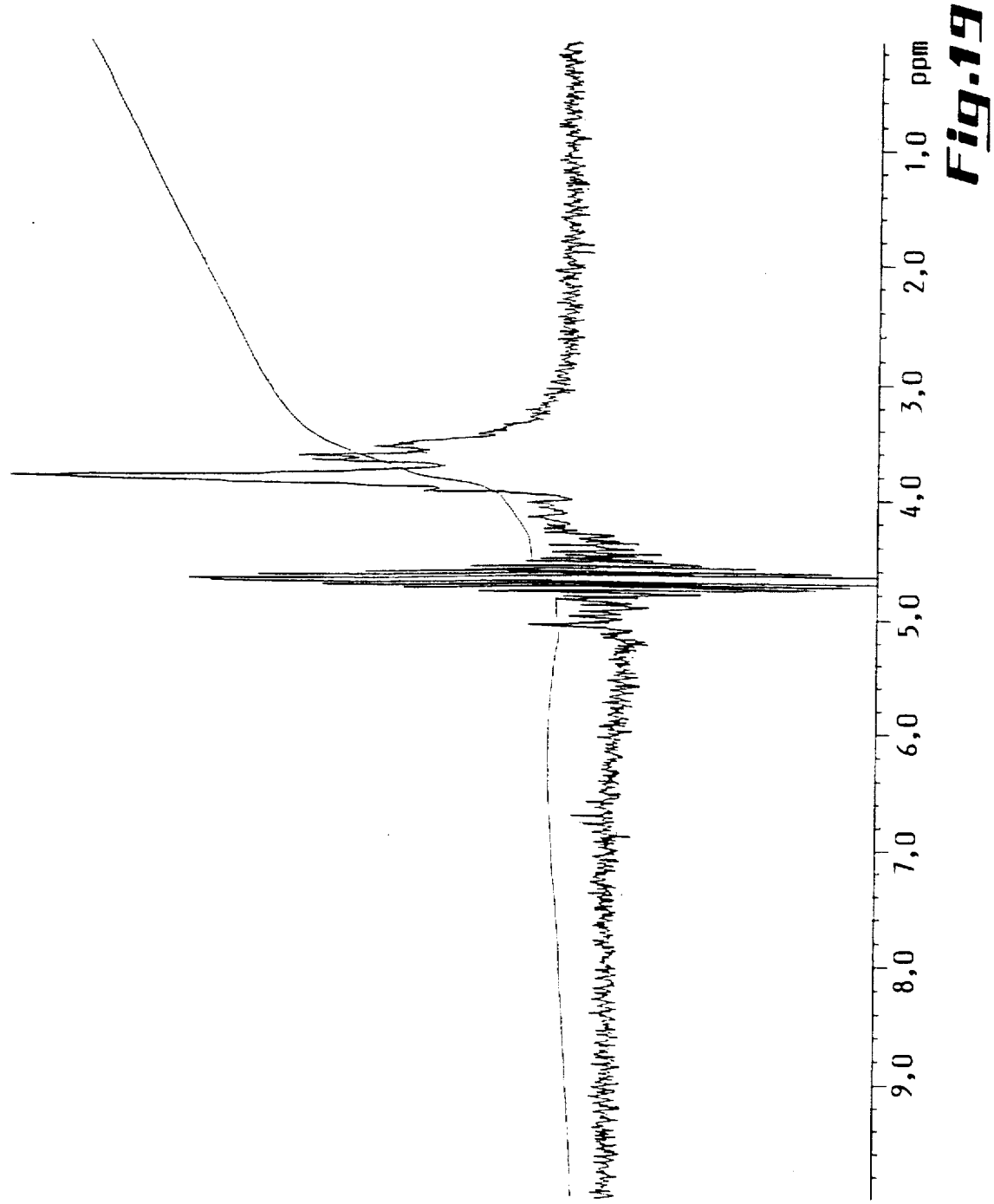

FIG. 19: 80 MHz $^1$H NMR spectrum of β-CD in $D_2O$ between 0 and 10 ppm.

Figure 20:
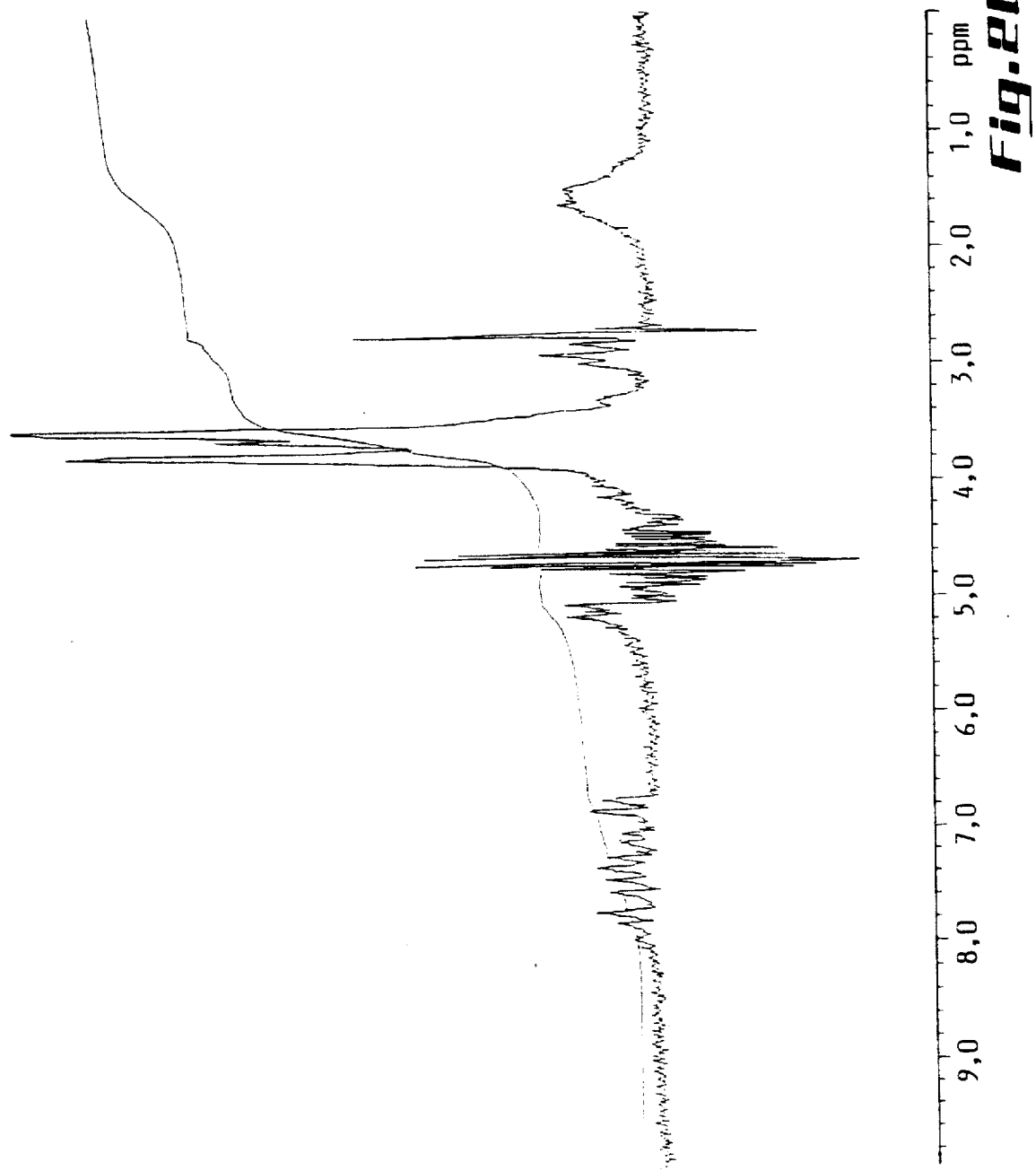

FIG. 20: 80 MHz $^1$H NMR spectrum of the nimesulide-L-lysine-β-CD complex in $D_2O$ between 0 and 10 ppm, in the presence of an excess of L-lysine.

The spectrum in FIG. 18 shows the presence of the aromatic protons of nimesulide between 7 and 8.5 ppm, of HOD at about 4.7 ppm and, at about 3 ppm, the presence of shielded protons of nimesulide (three methyl protons in the proximity of $SO_2N$) and of the methylene group ($CH_2$—N) of lysine. Other L-lysine protons are found at about 1.5–2 ppm.

The spectrum in FIG. 19 shows HOD at about 4.7 ppm and cyclodextrin protons at about 3–4 ppm.

The spectrum in FIG. 20 (complex) enables the different characteristic proton groups to be found, with a few shifts.

Figure 21:
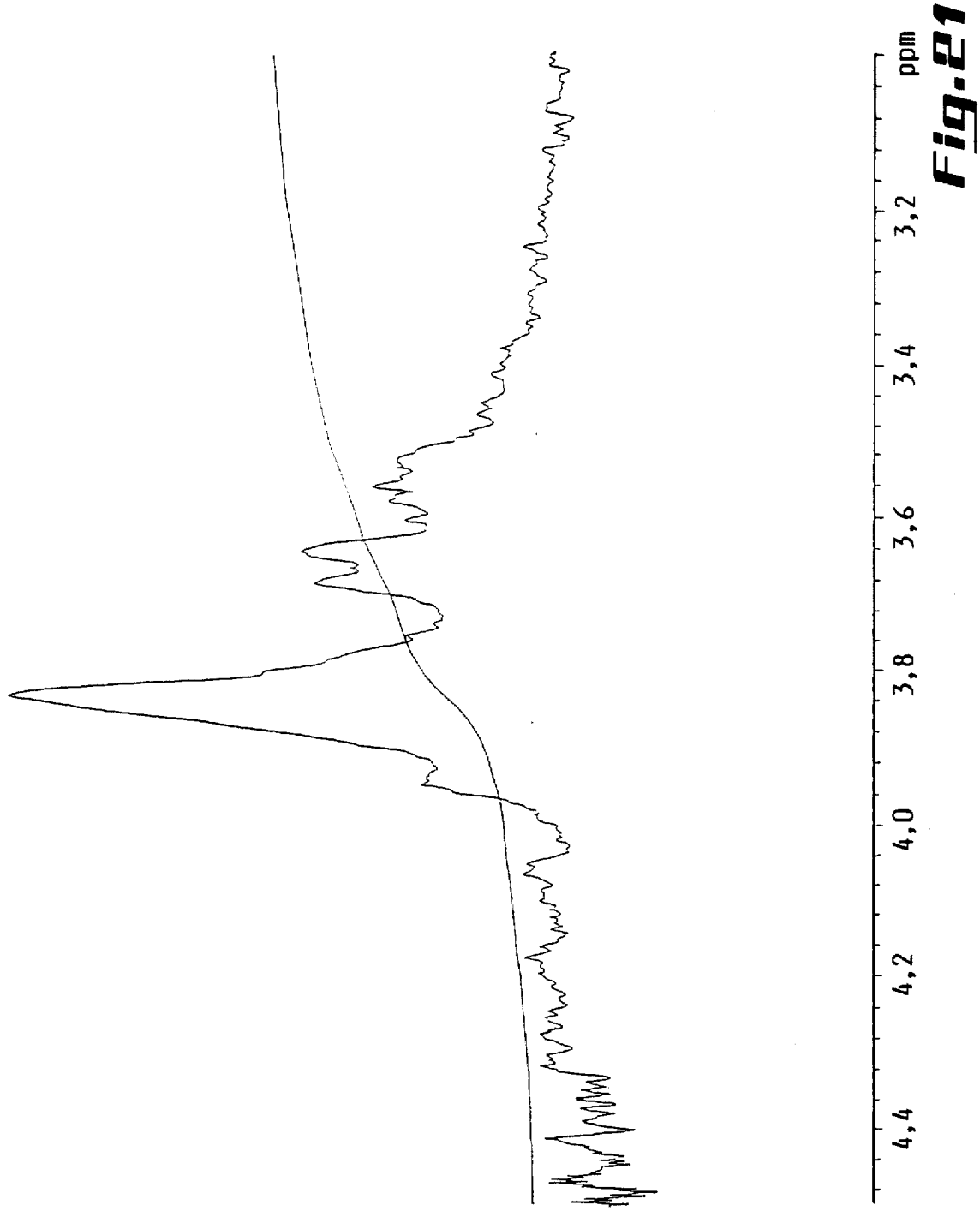
Figure 22:
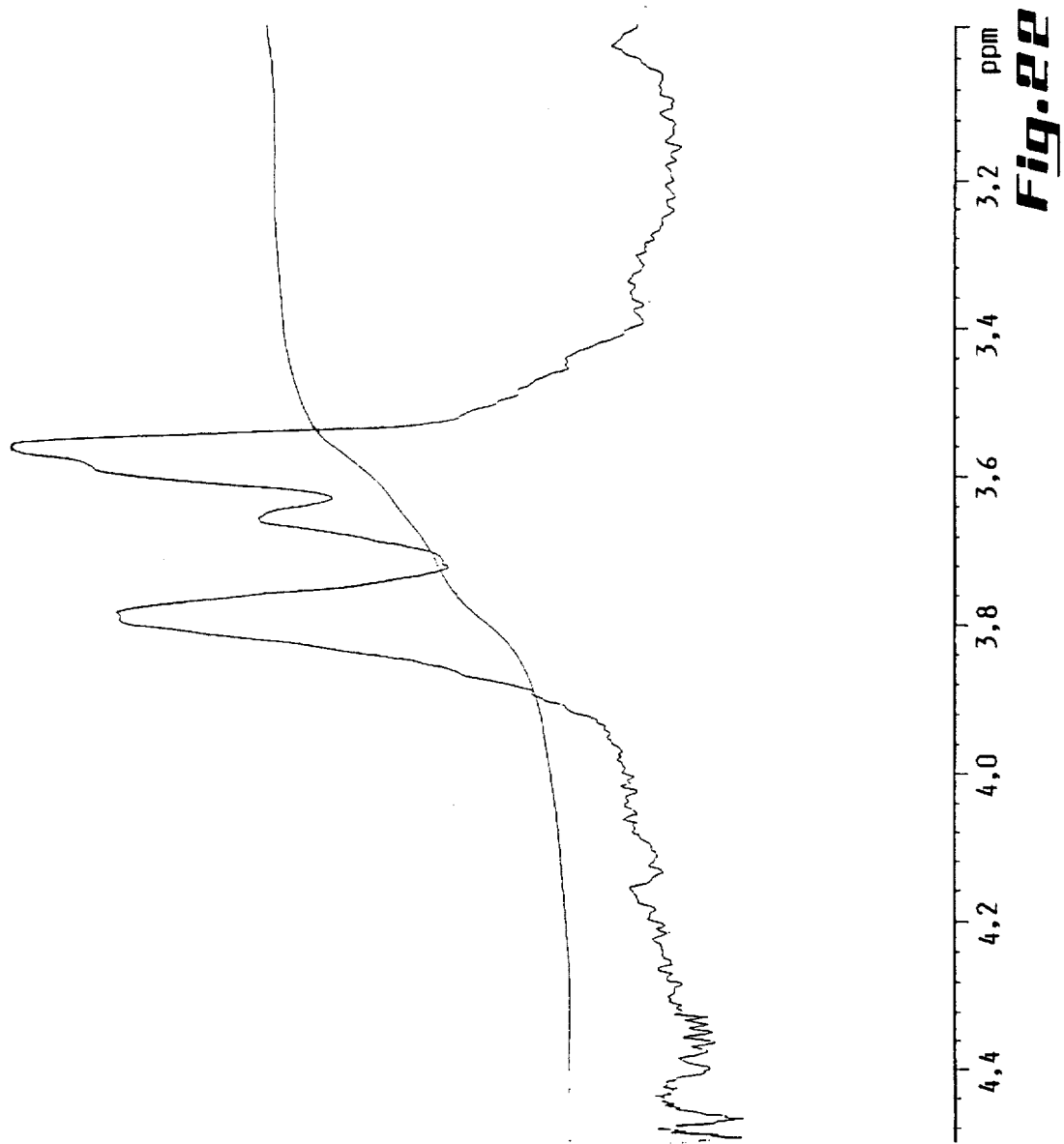

FIGS. 21 and 22 show the part between 3 and 4.5 ppm, characteristic of the protons of β-CD, and of β-CD and the complex respectively. Comparison of these spectra clearly shows the shift in the peaks which is due to the inclusion of nimesulide in β-CD.

Figure 23:
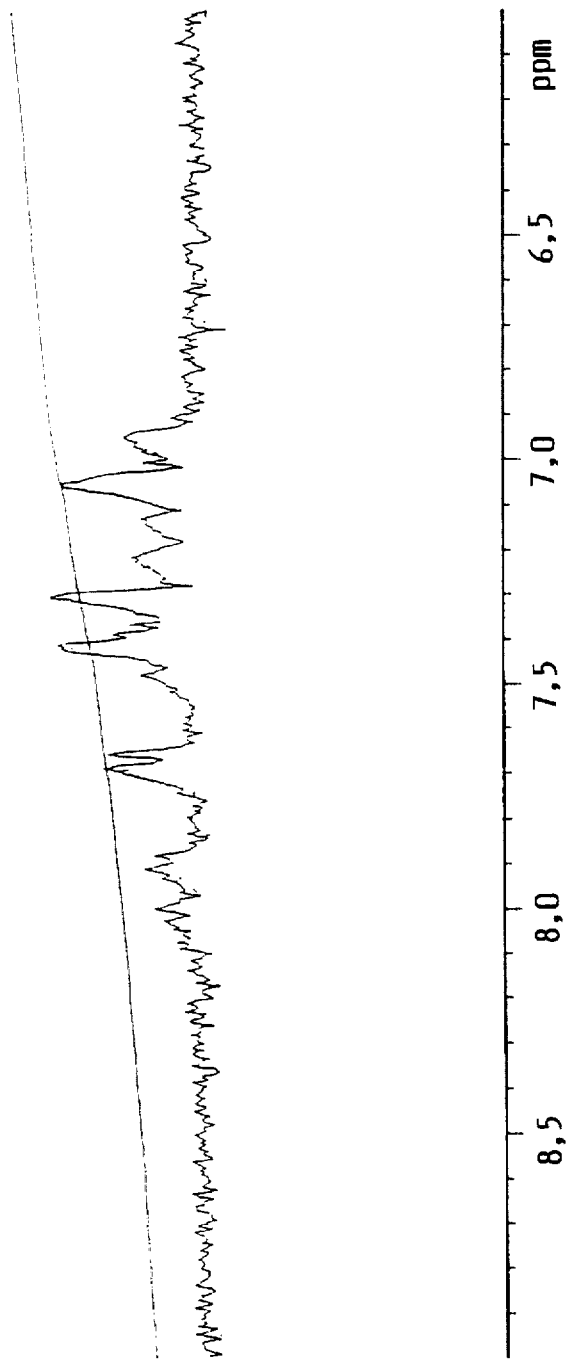
Figure 24:
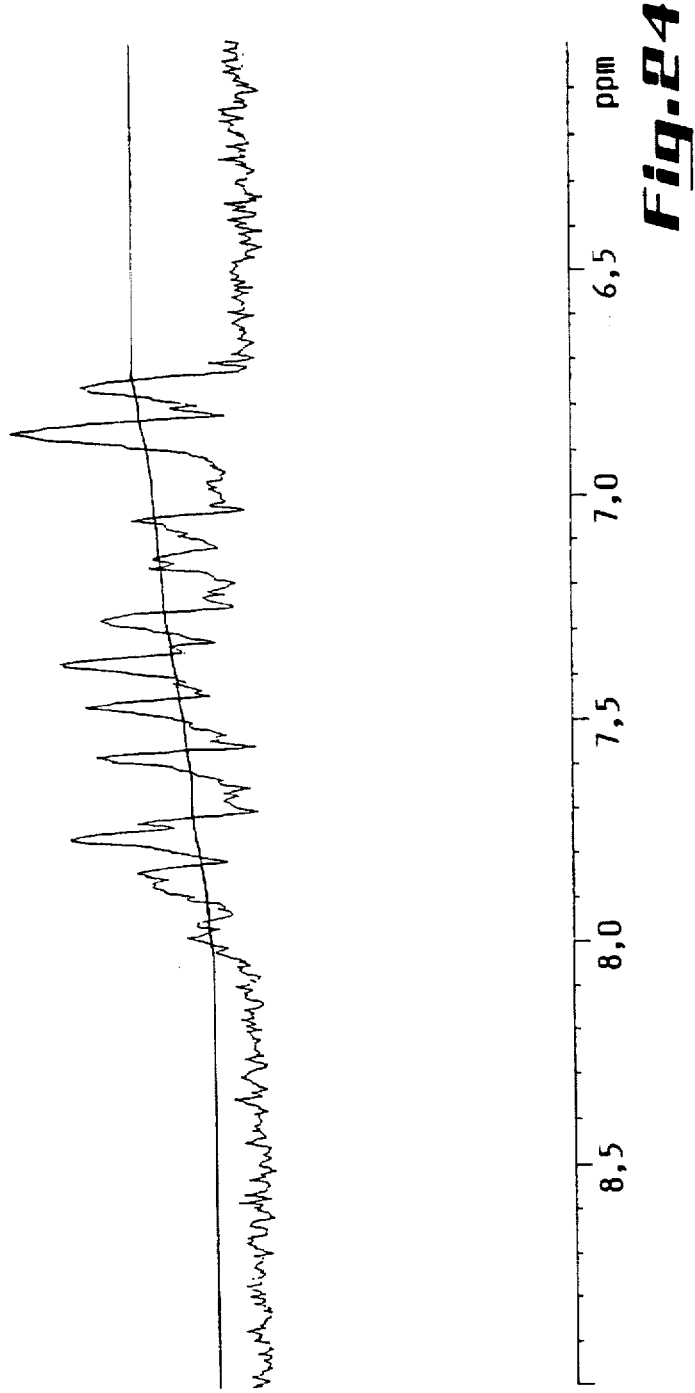

FIGS. 23 and 24 show the part between 6 and 9 ppm, characteristic of the protons of the aromatic nuclei of nimesulide. Comparison of these spectra shows the shift of the characteristic peaks of the aromatic protons of nimesulide.

Analyses by 400 MHz $^1$HNMR confirm these first results.

Figure 25:
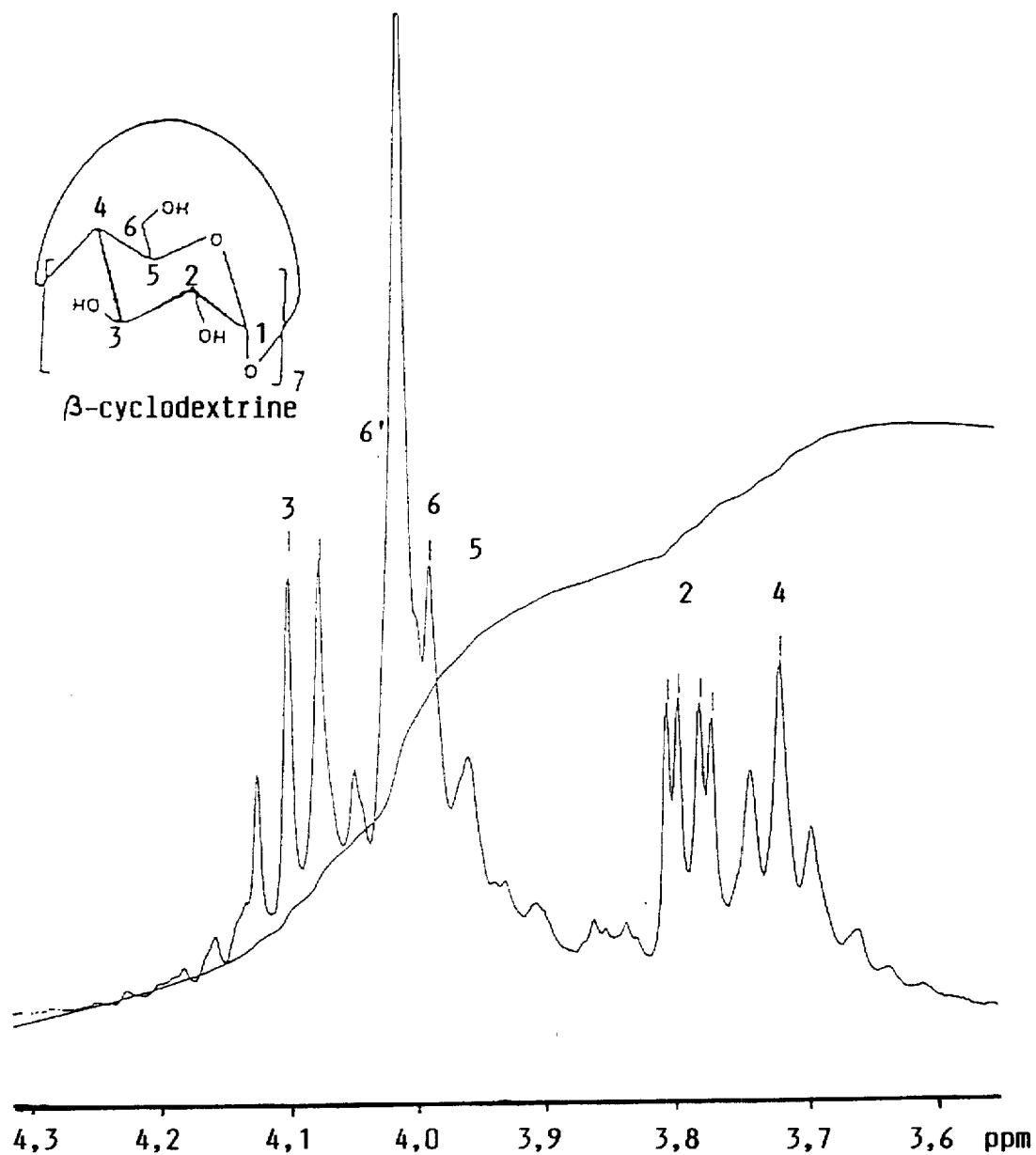

FIG. 25: 400 MHz $^1$HNMR spectrum of β-CD in $D_2O$.

Figure 26:
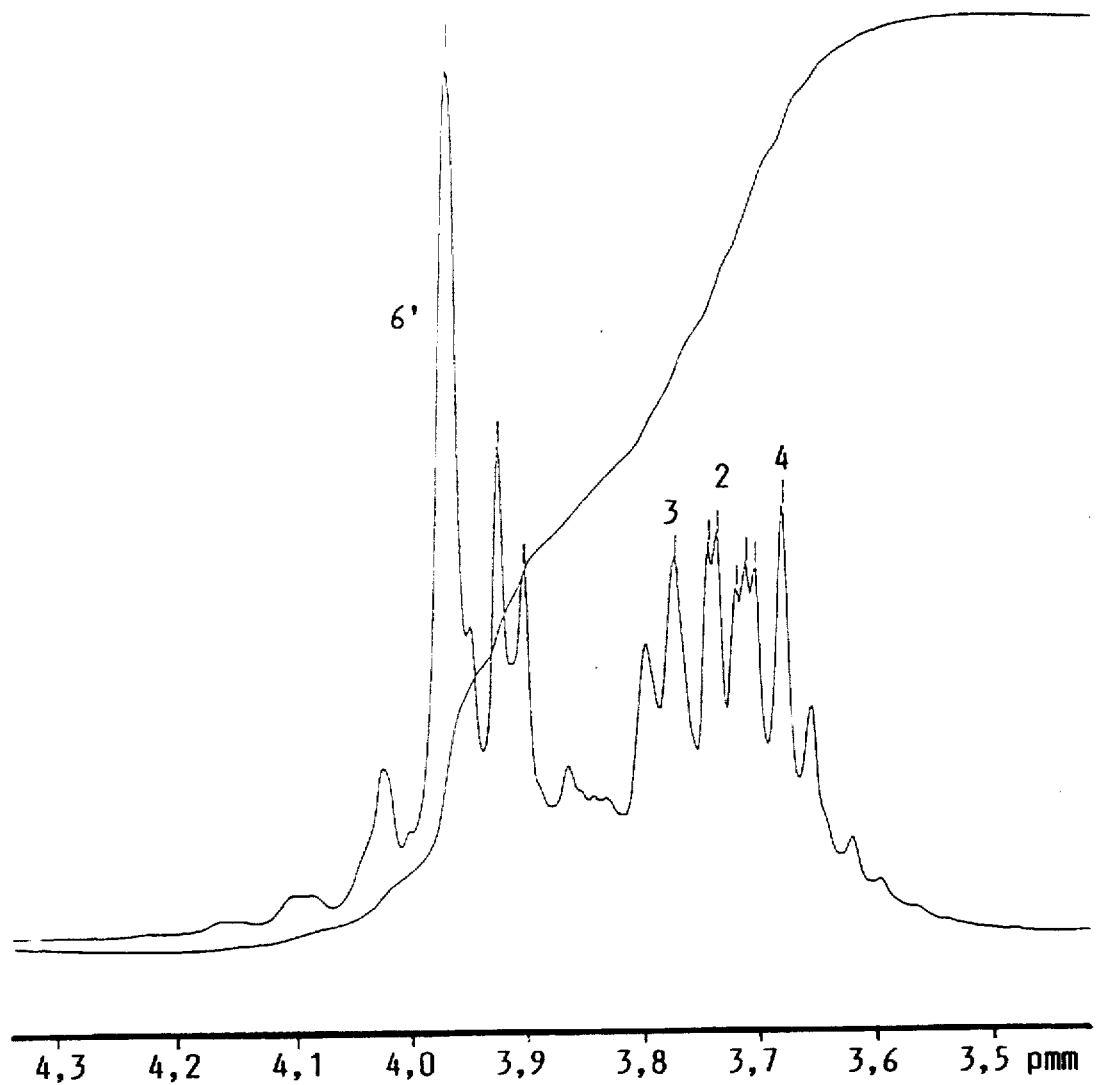

FIG. 26: 400 MHz $^1$HNMR spectrum of the 1/2/1 nimesulide-L-lysine-β-CD mixture in $D_2O$, part characteristic of β-CD.

FIG. 25 allows the different protons of β-CD to be distinguished. It is seen in FIG. 25 that the 3-H and 5-H protons are affected most. Now, behavior of this type is typical of the inclusion of aromatic molecules in cyclodextrins. In fact, 3-H and 5-H are the protons located inside the cyclodextrin cavity.

Figure 27:
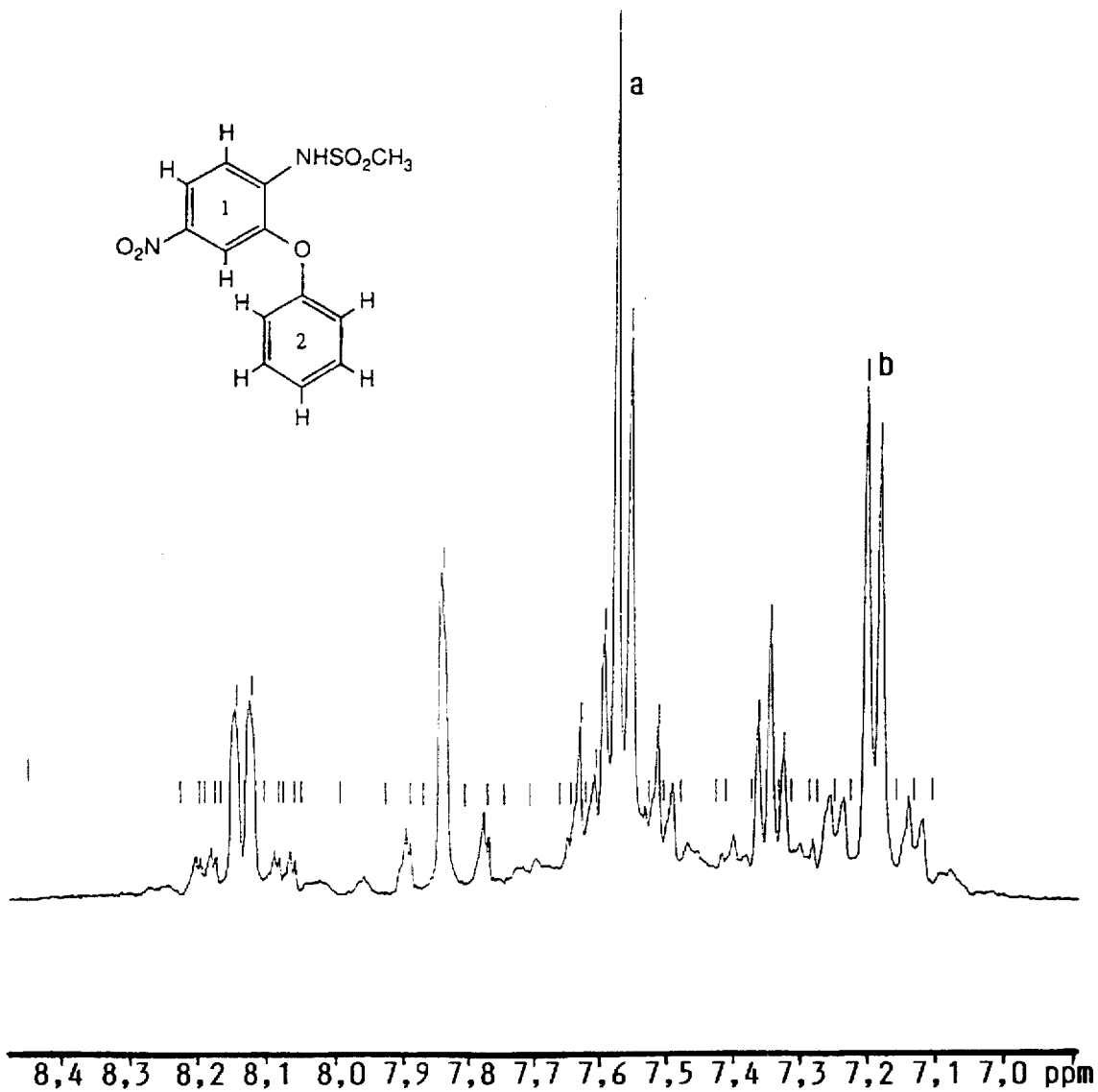

FIG. 27: 400 MHz $^1$HNMR spectrum of the nimesulide-L-lysine salt+excess of L-lysine, part characteristic of the aromatic part.

Figure 28:
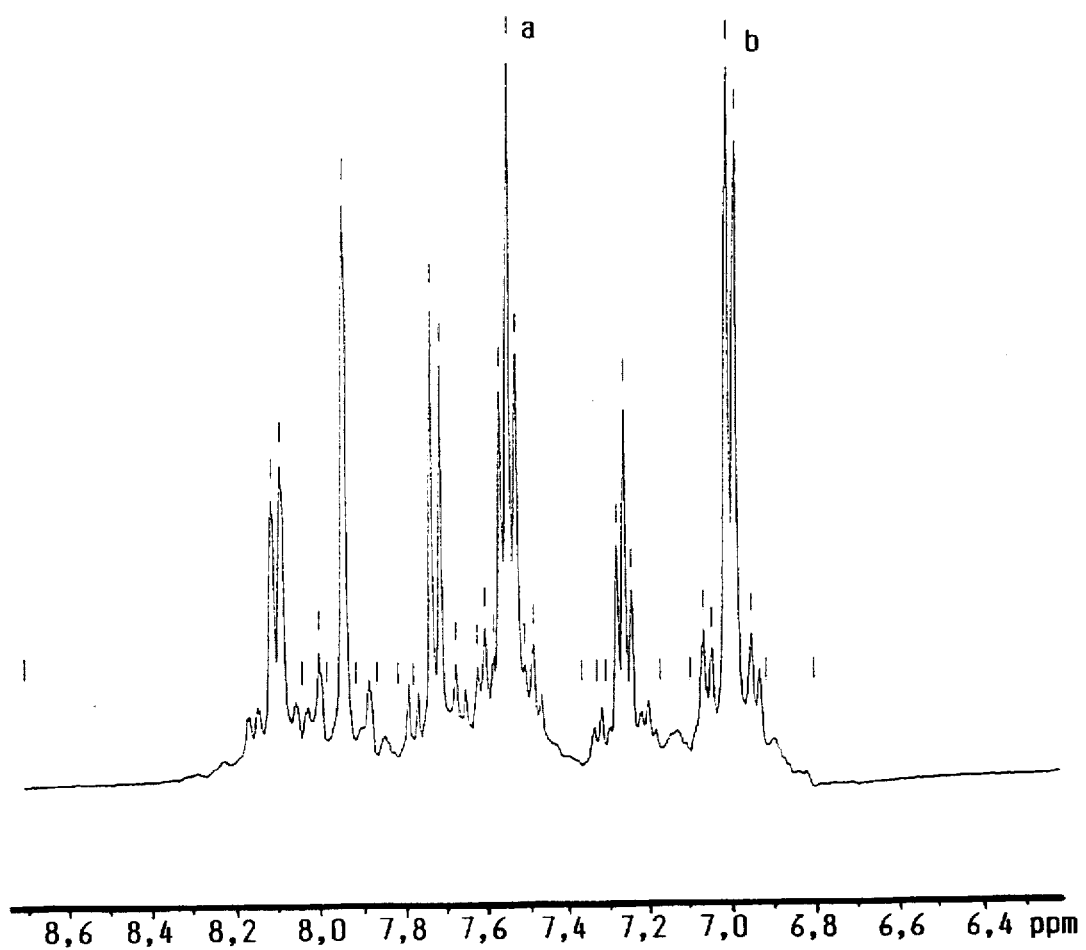

FIG. 28: 400 MHz $^1$HNMR spectrum of the 1/2/1 nimesulide-L-lysine-β-CD mixture.

Here, too, shifts are found in the characteristic protons of the aromatic parts of nimesulide. Ring No. 2 shows a group of protons of the AA'BB'C type which could be attributed to the groups of peaks a and b. Since these proton groups retain the same symmetry in the presence of β-CD, this means that ring 2 retains its free rotation and is therefore not included. It would therefore appear to be ring No. 1 that would be included in β-CD, in solution.

EXAMPLE 8

Comparison of the solubilities at different pH values

Table 2, which follows, compares the solubility as a function of the pH of nimesulide, of the nimesulide-L-lysine salt, of the nimesulide-L-lysine-β-CD (1/2/1) combination obtained by nebulization, of the nimesulide-L-lysine-γ-CD (1/2/1) combination obtained by nebulization and the solubility of mixtures of nimesulide-L-lysine salt with an additional equivalent of L-lysine and of β- or γ-CD in order to conform to the same proportions as the abovementioned combinations.

TABLE 2

Solubility expressed in μg of nimesulide per ml.

| | pH | | | | | |
|---|---|---|---|---|---|---|
| | 1.5 | 3.0 | 4.0 | 5.0 | 6.0 | 6.8 |
| nimesulide | 4.8 | 4.6 | 4.6 | 4.9 | 7.0 | 14.8 |
| nimesulide-L-lysine | 8.5 | 5.1 | 4.3 | 4.6 | 9.9 | 41.7 |
| Complexes: | | | | | | |
| nebulized 1/2/1 nimesulide-L-lysine-β-CD | 48.0 | 37.9 | 31.1 | 46.1 | 504.6 | 2373.0 |
| nebulized 1/2/1 nimesulide-L-lysine-γ-CD | 20.3 | 11.3 | 11.1 | 12.5 | 62.4 | 1711.2 |
| Physical mixtures: | | | | | | |
| nimesulide-L-lysine + L-lysine + β-CD | 31.9 | 21.2 | 24.8 | 45.1 | 470.9 | 2391.6 |
| nimesulide-L-lysine + L-lysine + γ-CD | 10.2 | 8.4 | 8.8 | 8.5 | 68.3 | 1766.2 |

It is found that complexes and physical mixtures yield comparable results. Complexing therefore takes place in situ, in solution. This is why L-lysine is also employed as a simple excipient.

EXAMPLE 9

Study of the influence of L-lysine on the increase in the solubility in water of a solid combination originating from the spray-drying of an ammoniacal aqueous solution of nimesulide and β-CD 20 g of nimesulide are dispersed in 350 ml of water. 85.4 g of β-CD are dispersed in 800 ml of distilled water. The two suspensions are combined and 20 ml of 16.7% ammoniacal solution are added. A solution is obtained which is nebulized in the following conditions:

Throughput: ±14 ml/min.

Entry temperature: 140°–150° C.

Exit temperature: 80° C.

The isolated product exhibits the following characteristics:

Bright yellow powder with an odor of aqueous ammonia.

Water content: 5.06%

Nimesulide content: 20.03%

$NH_3/NH_4^+$ content: 0.48%

2 g of the isolated product ($1.3 \times 10^{-3}$ mole of nimesulide) are suspended in 40 ml of water and kept at a temperature of 25° C. during the gradual addition of L-lysine monohydrate. Complete dissolution of the solid is reached when the quantity of L-lysine monohydrate is equal to 0.30 g±0.02 g ($1.8 \times 10^{-3}$ mole).

The same operation performed at 80° C. yields a comparable result (complete redissolution) with the addition of 0.21 g±0.02 g of L-lysine monohydrate ($1.3 \times 10^{-3}$ mole). The two yellow solutions stored for several days at ambient temperature do not leave any precipitate.

In this experiment it is again demonstrated that the simultaneous use of L-lysine and of cyclodextrin enables the solubility of nimesulide to be considerably improved.

A few nonlimiting examples of pharmaceutical compositions based on nimesulide in accordance with the present invention are given below.

EXAMPLE 10

Tablets or gelatin capsules containing 50 or 100 mg of nimesulide

|  | 50 mg of nimesulide | 100 mg of nimesulide |
| --- | --- | --- |
| Nimesulide-L-lysine-β-CD (1/2/1) complex | 266.5 mg | 533.0 mg |
| Calcium carbonate | 54.0 mg | 108.0 mg |
| Explotab (registered mark) (superdisintegrator) | 18.0 mg | 36.0 mg |
| Avicel PH 200 (registered mark) microcrystalline cellulose) | 18.0 mg | 36.0 mg |
| TOTAL: | 356.5 mg | 713 mg |

EXAMPLE 11

Tablets or gelatin capsules containing 50 or 100 mg of nimesulide

|  | 50 mg of nimesulide | 100 mg of nimesulide |
| --- | --- | --- |
| Nimesulide-L-lysine | 73.7 mg | 147.4 mg |
| β-Cyclodextrin | 184.2 mg | 368.5 mg |
| L-Lysine | 23.7 mg | 47.4 mg |
| Calcium carbonate | 57.1 mg | 114.2 mg |
| Explotab (registered mark) | 19.0 mg | 38.0 mg |
| Avicel PH 200 (registered mark) | 19.0 mg | 38.0 mg |
| TOTAL: | 376.7 mg | 753.4 mg |

EXAMPLE 12

Tablets or gelatin capsules containing 50 or 100 mg of nimesulide

|  | 50 mg of nimesulide | 100 mg of nimesulide |
| --- | --- | --- |
| Nimesulide | 50.0 mg | 100 mg |
| β-Cyclodextrin | 184.1 mg | 368.2 mg |
| L-Lysine | 47.4 mg | 94.8 mg |

-continued

|  | 50 mg of nimesulide | 100 mg of nimesulide |
| --- | --- | --- |
| Calcium carbonate | 57.1 mg | 114.2 mg |
| Explotab (registered mark) | 19.0 mg | 38.0 mg |
| Avicel PH 200 (registered mark) | 19.0 mg | 38.0 mg |
| TOTAL: | 376.6 mg | 753.2 mg |

EXAMPLE 13

Tablets or gelatin capsules containing 50 or 100 mg of nimesulide

|  | 50 mg of nimesulide | 100 mg of nimesulide |
| --- | --- | --- |
| Nimesulide β-CD | 249.6 mg | 499.2 mg |
| L-Lysine | 47.4 mg | 94.8 mg |
| Calcium carbonate | 57.1 mg | 114.2 mg |
| Explotab (registered mark) | 19.0 mg | 38.0 mg |
| Avicel PH 200 (registered mark) | 19.0 mg | 38.0 mg |
| TOTAL: | 392.1 mg | 784.2 mg |

Dry granulation of the constituents of Examples 10, 11, 12 and 13 yields a granulate which can be either compressed after addition of 1% of magnesium stearate or encapsulated in gelatin or else put into sachets:

| Granulate | equivalent to 50 mg of nimesulide | equivalent to 100 mg of nimesulide |
| --- | --- | --- |
| Sorbitol | 2500 mg | 4000 mg |
| Lemon essence | 15 mg | 30 mg |
| Na saccharin | 5 mg | 5 mg |

In the case of Examples 11, 12 and 13 the complex is formed in situ.

EXAMPLE 15

Oral liquid formulation

Nimesulide-L-lysine-β-CD (1/2/1) complex: 5.330 g

Hydroxypropyl cellulose: 0.600 g

Methylparaben: 0.210 g

Propylparaben: 0.090 g

Sodium saccharin: 0.100 g

Water sufficient quantity to make 300 ml

The hydroxypropyl cellulose is dissolved in is approximately 80 ml of lukewarm water containing the dissolved complex. The other additives are added so as to obtain a homogeneous solution. Each soupspoonful (15 ml) contains 50 mg of nimesulide.

EXAMPLE 16

Formulation of an injectable composition containing 5 mg/ml of nimesulide

Nimesulide-L-lysine-γ-CD (1/2/1) complex: 334.67 mg

NaCl: sufficient quantity to make an isotonic solution (±70 mg)

Water for injection: 10 ml

The γ-CD employed for the preparation is a γ-CD of pyrogen-free grade. The solution is introduced into a suitable bottle after sterilizing filtration.

The different formulations therefore apply either to the complexes directly or to the mixtures so as to form the soluble complex in situ.

Other formulations are also possible, such as suppositories or salves.

We claim:

1. A water-soluble nimesulide salt consisting of the reaction product of nimesulide and L-lysine.

2. The salt according to claim 1, wherein the salt contains 1 mole of L-lysine per mole of nimesulide.

3. An aqueous solution containing the nimesulide salt in accordance with claim 1 and L-arginine.

4. The solution according to claim 3, wherein the weight ratio of the nimesulide salt to the L-arginine is approximately 1:1.

5. A nimesulide-based composition, comprising a mixture of nimesulide, L-lysine and optionally L-arginine or a cyclodextrin.

6. A nimesulide-based composition, comprising the nimesulide-L-lysine salt in accordance with claim 1, in mixture with at least one cyclodextrin.

7. A nimesulide-based composition, comprising a complex of nimesulide with at least one cyclodextrin in mixture with L-lysine.

8. A nimesulide-based composition, comprising a nimesulide-L-lysine-cyclodextrin complex.

9. A composition in accordance with claim 5, wherein the cyclodextrin is selected from the group consisting of α-, β- and γ-cyclodextrins, their hydrates, their derivatives and their mixtures.

10. A composition in accordance with claim 9, wherein the cyclodextrin derivatives are selected from the group consisting of alkylated and hydroxyalkylated cyclodextrin derivatives.

11. A composition in accordance with claim 5, wherein the molar ratio of the nimesulide-L-lysine and cyclodextrin is from 1:1:1 to 1:2:1.

12. A process for the preparation of the water-soluble nimesulide salt in accordance with claim 1, the process comprising dissolving the nimesulide and L-lysine in methanol and separating methanol from the mixture thus obtained by a separation method.

13. The process in accordance with claim 12, wherein two separate methanolic solutions are prepared containing nimesulide and L-lysine respectively, which are then subsequently placed in contact with each other to obtain said mixture.

14. The process in accordance with claim 12, wherein the methanol is heated to a temperature close to its boiling point.

15. The process in accordance with claim 14, wherein the methanol is heated to a temperature of 54° to 64° C.

16. A pharmaceutical composition for the treatment of inflammatory disorders, comprising:

an effective quantity of the nimesulide salt in accordance with claim 1, in combination with at least one excipient.

17. The pharmaceutical composition in accordance with claim 16, wherein the composition contains L-lysine as said excipient.

18. A method of treating inflammatory disorders in a person in need thereof, the method comprising administering to said person a pharmaceutical composition in accordance with claim 16.

* * * * *